(12) United States Patent
Marshall et al.

(10) Patent No.: US 7,819,662 B2
(45) Date of Patent: Oct. 26, 2010

(54) MULTI-COMPONENT DENTAL APPLIANCES AND A METHOD FOR CONSTRUCTING THE SAME

(75) Inventors: Michael Craig Marshall, Prior Lake, MN (US); James Todd Ledin, Chanhassen, MN (US)

(73) Assignee: Geodigm Corporation, Chanhassen, MN (US)

( * ) Notice: Subject to any disclaimer, the term of this patent is extended or adjusted under 35 U.S.C. 154(b) by 173 days.

(21) Appl. No.: 11/186,391

(22) Filed: Jul. 20, 2005

(65) Prior Publication Data

US 2006/0115795 A1   Jun. 1, 2006

Related U.S. Application Data

(60) Provisional application No. 60/631,897, filed on Nov. 30, 2004.

(51) Int. Cl.
*A61C 5/08* (2006.01)
(52) U.S. Cl. .......................................... 433/218; 264/16
(58) Field of Classification Search ................. 433/218, 433/219, 223, 213–215, 202.1; 700/182, 700/97, 98, 117; 264/16–19, 20, 308
See application file for complete search history.

(56) References Cited

U.S. PATENT DOCUMENTS

| | | | |
|---|---|---|---|
| 1,733,895 A | 10/1929 | Matteson, Jr. | |
| 2,194,790 A | 3/1940 | Glück | 32/12 |
| 3,807,862 A | 4/1974 | Hatzenbuhler | |
| 4,081,019 A | 3/1978 | Kulig | |
| 4,206,545 A | 6/1980 | Lord | |
| 4,273,580 A | 6/1981 | Shoher et al. | 75/165 |
| 4,411,626 A | 10/1983 | Becker et al. | |
| 4,611,288 A | 9/1986 | Duret et al. | |
| 4,663,720 A | 5/1987 | Duret et al. | |
| 4,741,378 A | 5/1988 | Engelman et al. | |
| 4,742,464 A | 5/1988 | Duret et al. | |

(Continued)

FOREIGN PATENT DOCUMENTS

DE    36 26 789 A1    2/1998

(Continued)

OTHER PUBLICATIONS

Frank Hermanek, Finding the Lost Wax Process, Jan.-Feb. 2002, pp. 5 & 7.

(Continued)

*Primary Examiner*—Cris L Rodriguez
*Assistant Examiner*—Sunil K Singh
(74) *Attorney, Agent, or Firm*—Merchant & Gould P.C.

(57) ABSTRACT

Dental appliances including multiple components and a system and method for constructing the same are disclosed herein. The dental components are designed to fit together to form the dental appliance. The components of the dental appliance are electronically modeled, printed, and pressed sequentially, separately, or as a unitary piece. Forming the dental appliance from multiple components enables each component of the dental appliance to be formed from a different material, each material having different features associated with it. In various embodiments, different materials have different colors, textures, opacities, and transformation factors associated with them. Furthermore, each component can be formed from multiple components. In some other embodiments, a support structure is designed and constructed in order to minimize deformation of a dental component during fabrication of the component.

26 Claims, 23 Drawing Sheets

U.S. PATENT DOCUMENTS

| | | | |
|---|---|---|---|
| 4,778,386 A | 10/1988 | Spiry | |
| 4,844,144 A | 7/1989 | Murphy et al. | |
| 4,850,873 A | 7/1989 | Lazzara et al. | 433/220 |
| 4,869,666 A | 9/1989 | Talass | |
| 4,937,928 A | 7/1990 | van der Zel | |
| 4,952,149 A | 8/1990 | Duret et al. | |
| 4,972,897 A | 11/1990 | Thomas | |
| 5,004,037 A | 4/1991 | Castaldo | |
| 5,011,405 A | 4/1991 | Lemchen | |
| 5,027,281 A | 6/1991 | Rekow et al. | |
| 5,092,022 A | 3/1992 | Duret | |
| 5,121,333 A | 6/1992 | Riley et al. | |
| 5,139,419 A | 8/1992 | Andreiko et al. | |
| 5,232,361 A | 8/1993 | Sachdeva et al. | |
| 5,237,998 A | 8/1993 | Duret et al. | |
| 5,257,203 A | 10/1993 | Riley et al. | |
| 5,273,429 A | 12/1993 | Rekow et al. | |
| 5,338,198 A | 8/1994 | Wu et al. | |
| 5,368,478 A | 11/1994 | Andreiko et al. | |
| 5,378,154 A | 1/1995 | van der Zel | |
| 5,431,562 A | 7/1995 | Andreiko et al. | |
| 5,447,432 A | 9/1995 | Andreiko et al. | |
| 5,454,717 A | 10/1995 | Andreiko et al. | |
| RE35,169 E | 3/1996 | Lemchen et al. | |
| 5,518,397 A | 5/1996 | Andreiko et al. | |
| 5,588,832 A | 12/1996 | Farzin-Nia | |
| 5,683,243 A | 11/1997 | Andreiko et al. | |
| 5,690,490 A | 11/1997 | Cannon et al. | |
| 5,725,376 A | 3/1998 | Poirier | |
| 5,735,692 A | 4/1998 | Berger | |
| 5,909,765 A | 6/1999 | McDowell | |
| 6,015,289 A | 1/2000 | Andreiko et al. | |
| 6,042,374 A | 3/2000 | Farzin-Nia et al. | |
| 6,049,743 A | 4/2000 | Baba | |
| RE36,863 E | 9/2000 | Snyder | |
| 6,152,731 A | 11/2000 | Jordan et al. | |
| 6,174,168 B1* | 1/2001 | Dehoff et al. | 433/202.1 |
| 6,177,034 B1 | 1/2001 | Ferrone | |
| 6,217,334 B1 | 4/2001 | Hultgren | |
| 6,227,850 B1 | 5/2001 | Chishti et al. | |
| 6,283,753 B1 | 9/2001 | Willoughby | |
| 6,287,121 B1 | 9/2001 | Guiot et al. | |
| 6,287,490 B2 | 9/2001 | Rheinberger et al. | |
| 6,322,728 B1 | 11/2001 | Brodkin et al. | |
| 6,354,836 B1 | 3/2002 | Panzera et al. | |
| 6,371,761 B1 | 4/2002 | Cheang et al. | |
| 6,398,554 B1* | 6/2002 | Perot et al. | 433/223 |
| 6,409,504 B1 | 6/2002 | Jones et al. | |
| 6,460,594 B1 | 10/2002 | Lam | |
| 6,463,344 B1 | 10/2002 | Pavloskaia et al. | |
| 6,506,054 B2 | 1/2003 | Shoher et al. | |
| 6,532,299 B1 | 3/2003 | Sachdeva et al. | |
| 6,568,936 B2 | 5/2003 | MacDougald et al. | |
| 6,648,640 B2* | 11/2003 | Rubbert et al. | 433/24 |
| 6,648,645 B1 | 11/2003 | MacDougald et al. | |
| 6,667,112 B2* | 12/2003 | Prasad et al. | 428/552 |
| 6,691,764 B2 | 2/2004 | Embert et al. | |
| 6,835,066 B2 | 12/2004 | Iiyama et al. | |
| 6,915,178 B2 | 7/2005 | O'Brien et al. | |
| 7,228,191 B2 | 6/2007 | Hofmeister et al. | |
| 7,463,942 B2 | 12/2008 | O'Brien et al. | |
| 7,735,542 B2 | 6/2010 | Marshall et al. | |
| 2002/0015934 A1 | 2/2002 | Rubbert et al. | |
| 2002/0110786 A1 | 8/2002 | Diller | |
| 2004/0121291 A1 | 6/2004 | Knapp et al. | |
| 2004/0137408 A1 | 7/2004 | Embert et al. | |
| 2004/0204787 A1* | 10/2004 | Kopelman et al. | 700/182 |
| 2004/0220691 A1* | 11/2004 | Hofmeister et al. | 700/98 |
| 2004/0265770 A1 | 12/2004 | Chapoulaud et al. | |
| 2005/0177261 A1* | 8/2005 | Durbin et al. | 700/98 |
| 2005/0177266 A1 | 8/2005 | Kopelman et al. | |
| 2005/0236352 A1 | 10/2005 | Lee | |
| 2005/0251281 A1* | 11/2005 | O'Brien et al. | 700/119 |
| 2006/0106484 A1* | 5/2006 | Saliger et al. | 700/182 |
| 2006/0115793 A1* | 6/2006 | Kopelman et al. | 433/215 |
| 2006/0115795 A1 | 6/2006 | Marshall et al. | |
| 2006/0122719 A1 | 6/2006 | Kopelman et al. | |
| 2008/0131846 A1 | 6/2008 | Marshall et al. | |
| 2008/0142183 A1 | 6/2008 | Marshall et al. | |
| 2008/0220395 A1 | 9/2008 | Marshall et al. | |
| 2009/0087818 A1 | 4/2009 | O'Brien et al. | |
| 2009/0148816 A1 | 6/2009 | Marshall et al. | |

FOREIGN PATENT DOCUMENTS

| | | |
|---|---|---|
| EP | 0 316 106 A1 | 5/1989 |
| EP | 0 322 257 A2 | 6/1989 |
| EP | 0 426 363 A2 | 5/1991 |
| EP | 0 502 227 B1 | 11/1996 |
| EP | 0 781 625 A1 | 7/1997 |
| EP | 1 006 931 B1 | 6/2000 |
| FR | 2 593 384 A1 | 1/1986 |
| GB | 2 296 673 A | 7/1996 |
| JP | 5-49651 | 3/1993 |
| JP | 10-118097 | 5/1998 |
| WO | WO 94/10935 | 5/1994 |
| WO | WO 95/15731 | 6/1995 |
| WO | WO 02/19940 A1 | 3/2002 |
| WO | WO 02/076327 A1 | 10/2002 |

OTHER PUBLICATIONS www.cranstoncasting.com/process.htm.

Lewis, J., "Software beefs up tractor radiator-guard mount," *Design News*, vol. 54, No. 4, pp. 87-88 (Feb. 15, 1999) (1 page abstract).

Rotert, V., "How one rapid prototyping method is able to eliminate tooling for investment casting," *Proceedings of the 45th Annual Technical Meeting and Exhibition Investment Casting Institute*, Atlanta, Georgia (1997) (1 page abstract).

Weeden, B. et al., "Alternative methods for custom implant production utilizing a combination of rapid prototyping technology and conventional investment casting," *Proceedings of the 1996 15th Southern Biomedical Engineering Conference*, Dayton, Ohio (1996) (1 page abstract).

Wirtz, H. et al., "Investment casting shells in 1 day using selective laser sintering (SLS)," *Proceedings of the 24th BICTA Conference on Investment Casting*, Oxford, GB (1999) (1 page abstract).

Wu, M. et al., "Application of rapid prototyping and numerical simulation in titanium dental castings," *Computer Assisted Surgery & Rapid Prototyping in Medicine*, 5th Int. Workshop (1999) (1 page abstract).

Seymour et al., "Assessment of shoulder dimensions and angles of porcelain bonded to metal crown preparations," *The Journal of Prosthetic Dentistry* (1996) 75: 406-411.

Cad Cam Ventures, Auto-Milled Crown and the Cad Cam Ventures, 13 pages (Feb. 1999).

Cicero, It's Time for Digital Solutions, Brochure, 12 pages (Apr. 1999).

DCS Dental AG, The Precident System, 16 pages (Apr. 1999).

Dentalmatic Technologies, Inc., "Premiering a Dental Lab Tool that Eliminates Waxing, Investing, Casting, Increases Productivity and Improves Labor Efficiency," 8 pages (Publicly known at least as early as Sep. 6, 2000).

Denzir, "Denzir—for Superior Dental Restorations!," 14 pages (Publicly known at least as early as Sep. 6, 2000).

Model Maker II, Sanders Prototype, Inc., The High Precision 3-D Modeling System, Brochure, 10 pages (Jul. 2000).

Sohmura et al., "Use of CAD/CAM system to fabricate dental prostheses. Part 1: CAD for a clinical crown restoration," *The International Journal of Prosthodontics*, vol. 8, No. 3, pp. 252-258 (1995).

Tamura, K., "Procelain-Fused-to-Metal Crowns," *Essential of Dental Technology*, pp. 356-359 (1987).

* cited by examiner

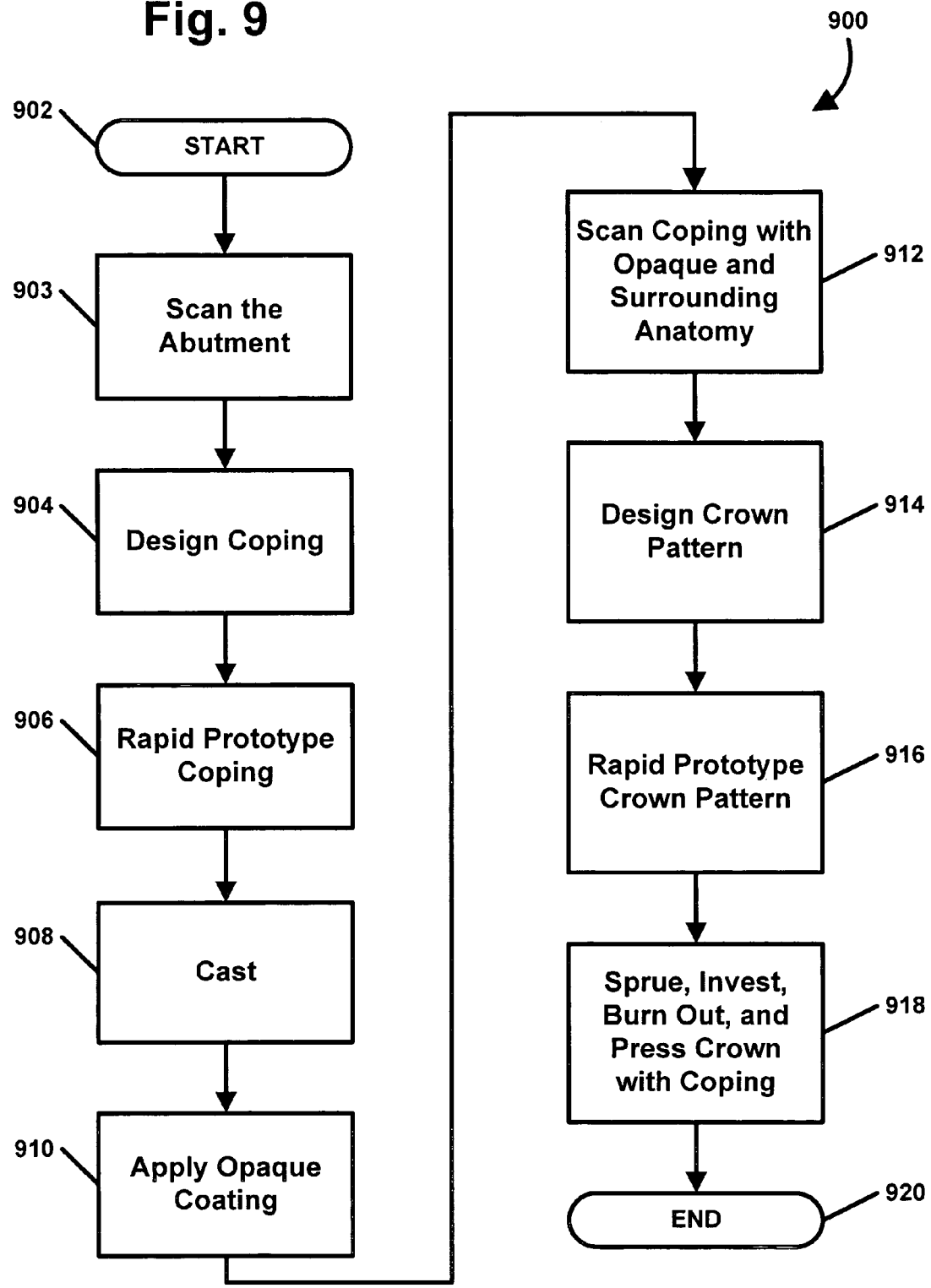

MULTI-COMPONENT DENTAL APPLIANCES AND A METHOD FOR CONSTRUCTING THE SAME

This application claims priority from provisional application Ser. No. 60/631,897, filed Nov. 30, 2004, and which is incorporated herein by reference.

TECHNICAL FIELD

This application relates generally to a dental appliance having multiple components and a method and system for constructing the dental appliance using electronic models; more particularly to a method and system for creating dental appliances that include components formed from different materials; and still more particularly to a method and system for creating personally tailored dental restorations, bridges, and implants using electronic modeling, rapid prototyping, and lost-wax techniques.

BACKGROUND OF THE INVENTION

Computer based systems that allow the creation and use of electronic models of teeth impressions to design some types of dental appliances have been developed over time. Dental appliances include, by way of illustration, restorations, bridges, and implants. Restorations include, by way of illustration, replacements for single teeth including incisors, molars, and pre-molars. Dental appliances are designed to mount to either natural teeth or implanted teeth substitutes. For the sake of convenience, this disclosure will use the term "abutment" to refer to both natural teeth and implanted teeth substitutes.

In some prior systems, an electronic model for a dental restoration is designed to complement an electronic image of an abutment. The electronic image of the abutment can be generated based on a patient's actual abutment or a study cast thereof. The electronic image is then printed in wax using a rapid prototyping machine and cast or pressed using a standard lost-wax manufacturing process. However, these systems generally construct dental restorations as single-piece physical objects fabricated using a single type of material such as gold or ceramic. Furthermore, the wax models are susceptible to warping and deformation when exposed to high temperatures or physical force.

In some other prior systems, dental appliances are constructed by hand from multiple components. These components are designed, sculpted, and fabricated as separate items that are then mated into a single physical structure. Creating these components as separate items makes mating and matching these components difficult. The ability to mate these separate components into a single structure depends upon the skill of the designer or fabricator to construct complimentary components.

An anterior restoration (i.e., a restoration of an incisor or pre-molar) is one example of a dental appliance made by hand in previous systems. Anterior restorations are more visible to onlookers and so greater care is generally taken in their creation to ensure the restoration resembles a natural tooth as much as possible. For example, color may vary over the length or width of a natural tooth. Teeth are generally darker in color closer to the gums. Furthermore, calcium deposits or staining may cause discoloration on the enamel of the tooth. In addition, color striations, often referred to as the Stria of Retzius, are caused by grooves or other such recesses formed in the enamel of the tooth during development. The resulting variation in thickness of the enamel causes an onlooker to see variations in color in the enamel of the tooth. One current solution for creating anterior restorations relies generally on hand painting each restoration to match the patient's other teeth.

The present invention addresses the above and other limitations of prior dental electronic modeling systems.

SUMMARY OF THE INVENTION

The invention relates to dental appliances including multiple components and a system and method for constructing the same. Dental components are designed to fit together to form a dental appliance configured to mount onto one or more of a patient's abutments. The components of the dental appliance are electronically modeled, printed, and pressed sequentially, separately, or as a unitary piece. Forming the dental appliance from multiple components enables each component of the dental appliance to be formed from a different material, each material having different features associated with it.

In various embodiments, different materials have different colors, textures, opacities, and transformation factors associated with them. Furthermore, each component can be formed from multiple components. Non-limiting examples of dental components include a coping substructure, a pontic, an abutment, a crown, a crown shell, and a post.

In some embodiments, a dental component, such as a crown or crown shell, includes geometric shapes or cutouts forming color striations.

In some other embodiments, a support structure is designed and constructed in order to minimize deformation of a dental component during fabrication of the component. The support structure acts as a spacer holding the walls of a printed component wax model in place. The support structure is typically unitary in construction with the printed wax model. In various examples, the support structure includes spokes, a hub, and/or a frame.

The method for constructing dental appliances having multiple components includes generating a first electronic model of a first dental component, printing a first wax model of the first dental component based on the electronic model, and casting or pressing the first wax model to form a first cast dental component. The method further includes generating a second electronic model of a second dental component designed to mate with the first dental component, printing a second wax model of the second dental component, and casting or pressing the second wax model onto the first cast dental component.

In some embodiments, the method further includes transforming an electronic model of a dental component such that dimensions of the transformed electronic model differ from desired dimensions of the dental component by a transformation factor, and fabricating the dental component using a material that changes in dimension during fabrication according to the transformation factor. This feature allows the invention to account for deficiencies in the casting materials.

In some embodiments, the method further includes electronically modeling and printing a support structure for minimizing deformation to the printed wax models. The support structure is typically unitary in construction with the printed wax model.

Example methods of generating electronic models include designing, selecting, transforming, and merging various polygonal meshes. Methods of printing component wax models include rapid prototyping wax models based on the electronic models. Methods of casting or pressing these wax models include lost-wax manufacturing techniques.

These and various other features and advantages will be apparent from a reading of the following detailed description and a review of the associated drawings.

BRIEF DESCRIPTION OF THE DRAWINGS

Referring now to the drawings:

FIG. 9 illustrates an operational flow for modeling and fabricating a dental restoration in accordance with one embodiment of the disclosure.

DETAILED DESCRIPTION OF THE PREFERRED EMBODIMENT

This application relates in general to a method and system for creating dental appliances using electronic modeling; and more particularly to a method and system for constructing restorations, bridges, implants, and other such dental appliances including a coping substructure using electronic modeling, rapid prototyping, and lost-wax manufacturing processes.

Figure 1:
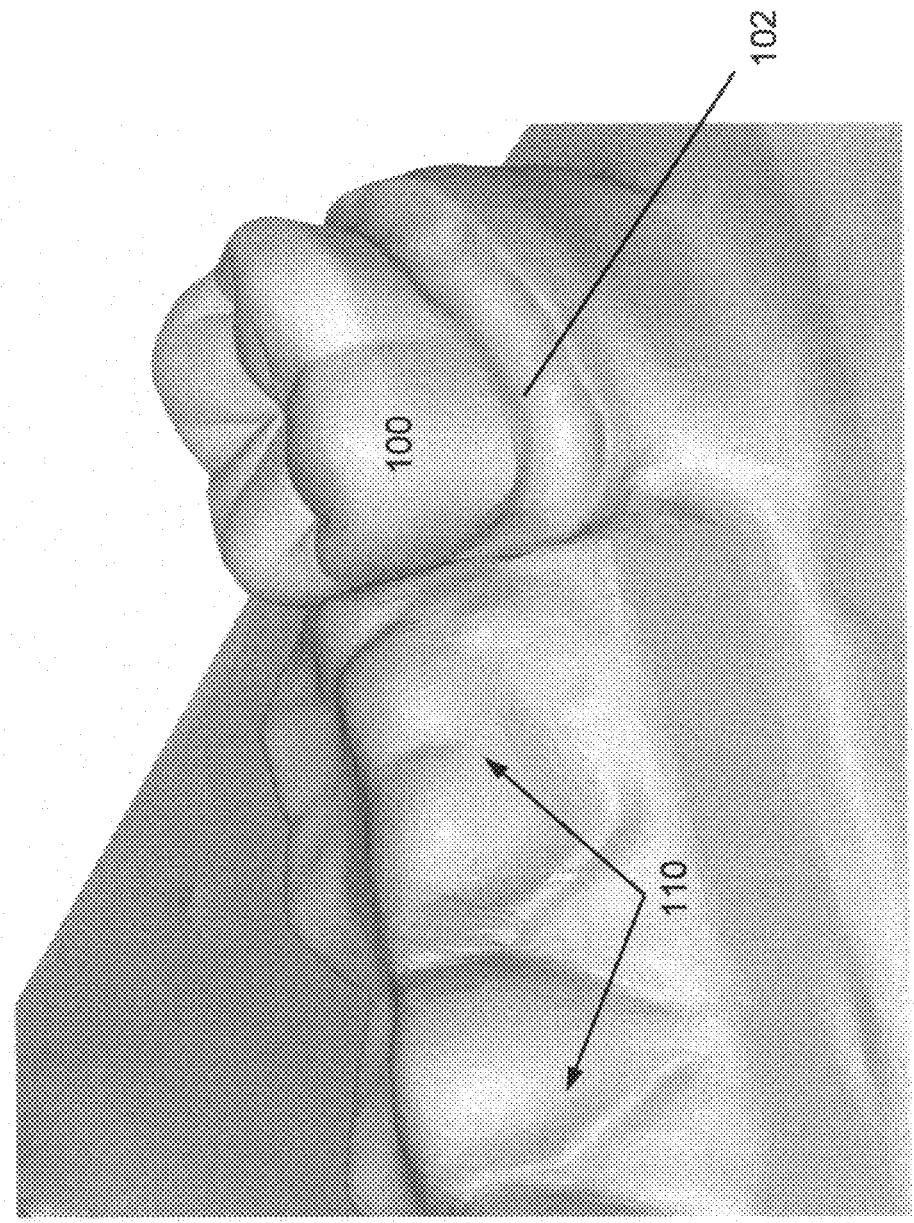
FIG. 1 illustrates an example of an electronic model for a dental restoration constructed according to one embodiment of the disclosure.

FIG. 1 illustrates an example of an electronic model for a dental restoration constructed according to one embodiment of the disclosure. In this example embodiment, a completed electronic model 100 of a restoration is shown positioned on an electronic model 102 of an abutment as it would be installed on a patient's actual abutment. The electronic model 102 of the abutment corresponds to a polygonal mesh created from scanning a portion of the patient's dentition 110. In one embodiment, the dentition 110 is scanned from a dental impression, otherwise known as a study cast. In another embodiment, the dentition 110 is scanned directly from the patient. In various embodiments, the electronic model 102 of the abutment includes adjacent and/or antagonistic teeth.

The electronic models 100, 102 consist of polygonal meshes. According to one embodiment, the electronic models 100, 102 are created using the processes described in commonly assigned U.S. Provisional Patent Application, "Method and Apparatus for Computer Generation of Electronic Model Images" Ser. No. 60/351,270, filed Jan. 27, 2002, now U.S. patent application, "Method and Apparatus for Computer Generation of Electronic Model Images" Ser. No. 10/305,302, filed Jan. 22, 2003, incorporated herein by reference. However, any suitable method for generating electronic models may be used.

Additionally, the electronic models 100, 102 may also be created using computed tomography (CT) scans of dental impressions, using commercially available CT scanning processes such as a process developed by Hytec Corp. of Los Alomos, N. Mex. Other methods of generating electronic models include optical system scanning, physical touch scanning, and any other such method. The generated polygonal meshes are used in subsequent processing independent of the source of the electronic models.

The electronic model 100 for the restoration (i.e., or any such dental appliance) is designed to mate with the surface of the electronic model 102 of the abutment. According to one embodiment the dental appliance includes a crown and coping substructure. Once designed, these components are fabricated and installed on the abutment of the patient. In one embodiment, a dental appliance fabrication process includes specifying the dental appliance in a standard Stereo lithography (STL) specification file, printing a wax model of the dental appliance using rapid prototyping processes, and casting or pressing the dental appliance using lost wax manufacturing techniques. One example of a rapid prototyping machine used to print wax models is the Patternmaster wax printer from Solidscape of Connecticut. However, any type of rapid prototyping process may be used without deviating from the spirit and scope of the disclosure. Example embodiments will now be illustrated using the generation of various dental appliances.

Figure 2:
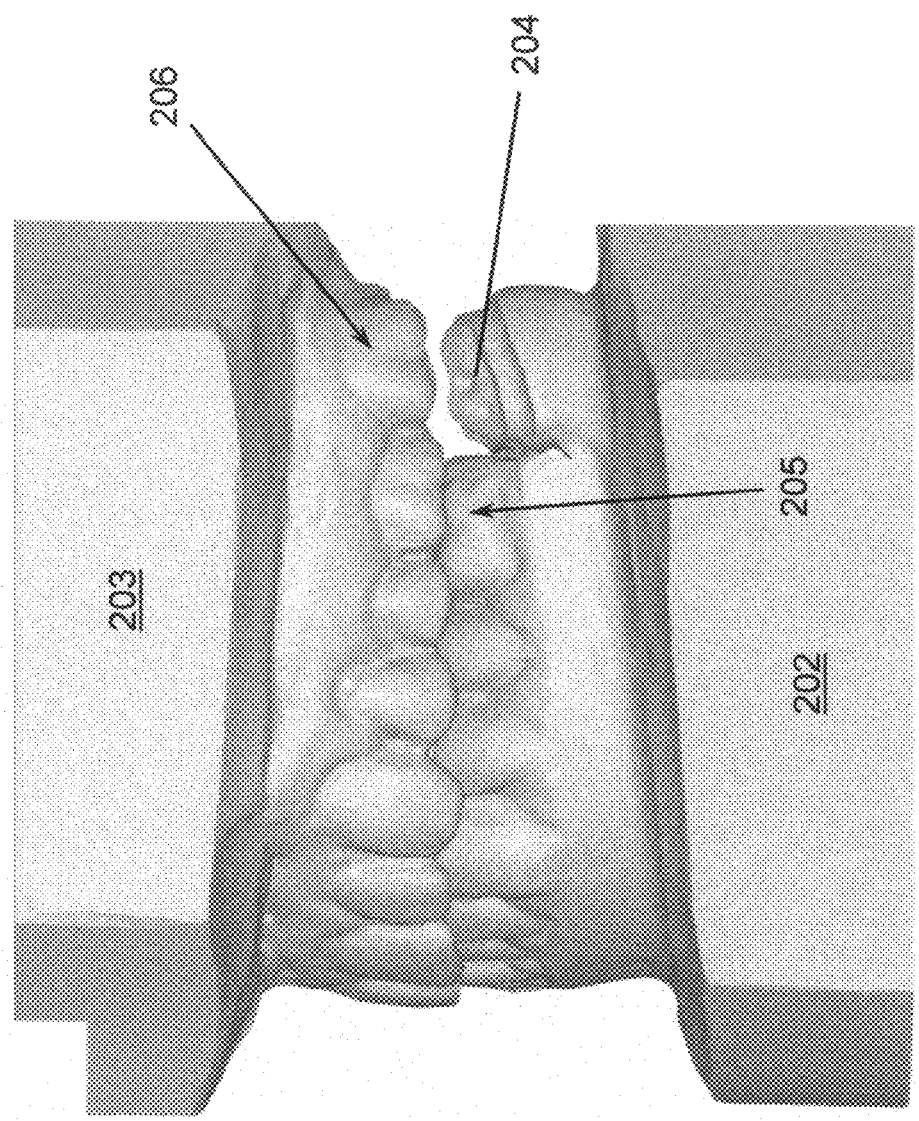
FIG. 2 illustrates a side view of an electronic model of a patient's dentition including an abutment according to one embodiment of the disclosure.

FIG. 2 illustrates a side view of an electronic model of a patient's dentition according to one embodiment of the disclosure. The electronic model includes a mandibular dentition 202 and a maxillary dentition 203. The mandibular dentition 202 includes an abutment 204 that represents the location on which a dental appliance is to be installed. The maxillary dentition 203 is positioned relative to the mandibular dentition 202 to simulate the interaction of the opposing dentitions while in centric occlusion or any such bite position. Adjacent tooth 205 is located next to the abutment 204 while antagonistic tooth 206 is in occlusion with the abutment 204. In some embodiments, the maxillary dentition 203 and the mandibular dentition 202 of the electronic model are moved relative to one another to permit the study of the interaction of opposing teeth during articulation of a patient's jaws.

Figure 3:
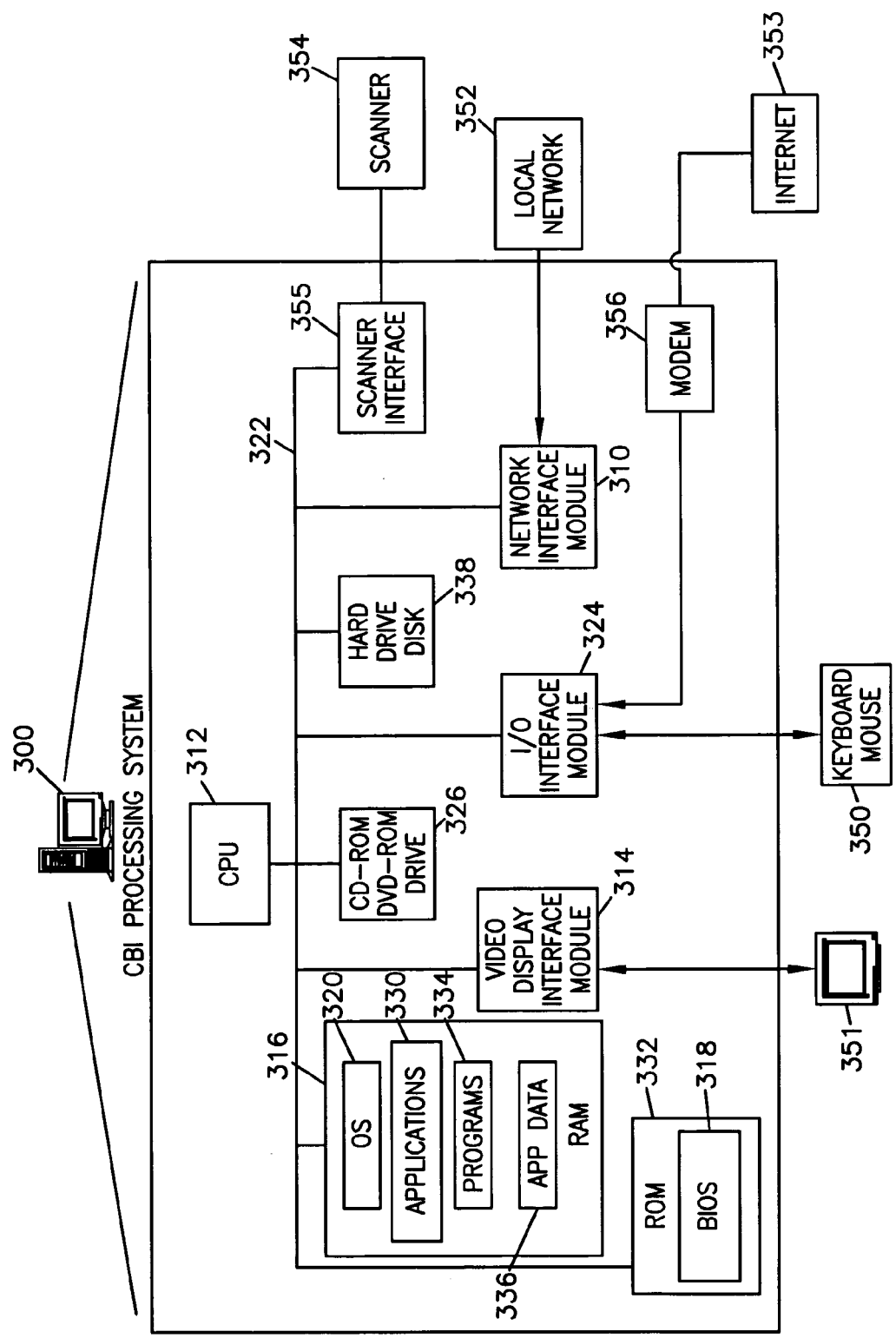
FIG. 3 illustrates a general purpose computing system for use in implementing one or more computing embodiments of the disclosure.

With reference to FIG. 3, an exemplary system for implementing the invention includes a general-purpose computing device in the form of a conventional personal computer 300, including a processor unit 312, read only memory (ROM) 332, random access memory (RAM) 316, and a system bus 322 that couples various system components including the RAM 316 to the processor unit 312. The system bus 322 may be any of several types of bus structures including a memory bus or memory controller, a peripheral bus and a local bus using any of a variety of bus architectures. A basic input/output system 318 (BIOS), which contains basic routines that help transfer information between elements within the personal computer 300, is stored in ROM 332.

The personal computer 300 further includes a hard disk drive 338 for reading from and writing to a hard disk (not shown), a magnetic disk drive (not shown) for reading from or writing to a removable magnetic disk, and an optical disk drive 326 for reading from or writing to a removable optical disk such as a CD ROM, DVD, or other optical media. The hard disk drive 338, magnetic disk drive, and optical disk drive 326 are connected to the system bus 322 by a hard disk drive interface (not shown), a magnetic disk drive interface (not shown), and an optical drive interface (not shown), respectively. The drives and their associated computer-readable media provide nonvolatile storage of computer readable instructions, data structures, programs, and other data for the personal computer 300.

Although the exemplary environment described herein employs a hard disk drive 338, a removable magnetic disk, and removable optical disk drive 326, other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs).

A number of program modules may be stored on the hard disk drive 338, magnetic disk drive, optical disk drive 326, ROM 332 or RAM 316, including an operating system 320, one or more application programs 330, other program modules 334, and program (i.e., application) data 336. A user may enter commands and information into the personal computer 300 through input devices such as a keyboard and/or mouse 350 (or other pointing device). Examples of other input devices may include a microphone, joystick, game pad, satellite dish, and scanner. These and other input devices are often connected to the processing unit 312 through a I/O port interface 324 that is coupled to the system bus 332. Nevertheless, these input devices also may be connected by other interfaces, such as a parallel port, game port, or a universal serial bus (USB). A monitor 351 or other type of display device is also connected to the system bus 332 via an interface, such as a video adapter 314. In addition to the monitor, personal computers typically include other peripheral output devices (not shown), such as speakers and printers.

The personal computer 300 may operate in a networked environment using logical connections to one or more remote computers. The remote computer may be another personal computer, a server, a router, a network PC, a peer device or other common network node, and typically includes many or all of the elements described above relative to the personal computer 300. The network connections include a local area network (LAN) and a wide area network (WAN). Such networking environments are commonplace in offices, enterprise-wide computer networks, intranets, and the Internet.

When used in a LAN networking environment, the personal computer 300 is connected to the local network 352 through a network interface or adapter 310. When used in a WAN networking environment, the personal computer 300 typically includes a modem or other means for establishing communications over the wide area network, such as the Internet 353. The modem 356, which may be internal or external, is connected to the system bus 332 via the I/O port interface 324. In a networked environment, program modules depicted relative to the personal computer 300, or portions thereof, may be stored in the remote memory storage device. It will be appreciated that the network connections shown are exemplary, and other means of establishing a communications link between the computers may be used.

A scanner 354 is connected to the computer 300 via an appropriate scanner interface 355. The scanner interface 355 is connected to the bus 322 such that the scanned data may be stored in the appropriate or desired memory location, manipulated by the CPU 312, displayed on the display 351, etc. Preferred scanners include a laser line scanner arranged and configured for scanning dental study casts. However, any suitable scanner may be used and a number of other methodologies might be employed to generate the scanned image data.

Portions of the preferred embodiment constructed in accordance with the principles of the present invention utilize a computer and are described herein as implemented by logical operations performed by a computer. The logical operations of these various computer implemented processes are generally performed either (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 4:
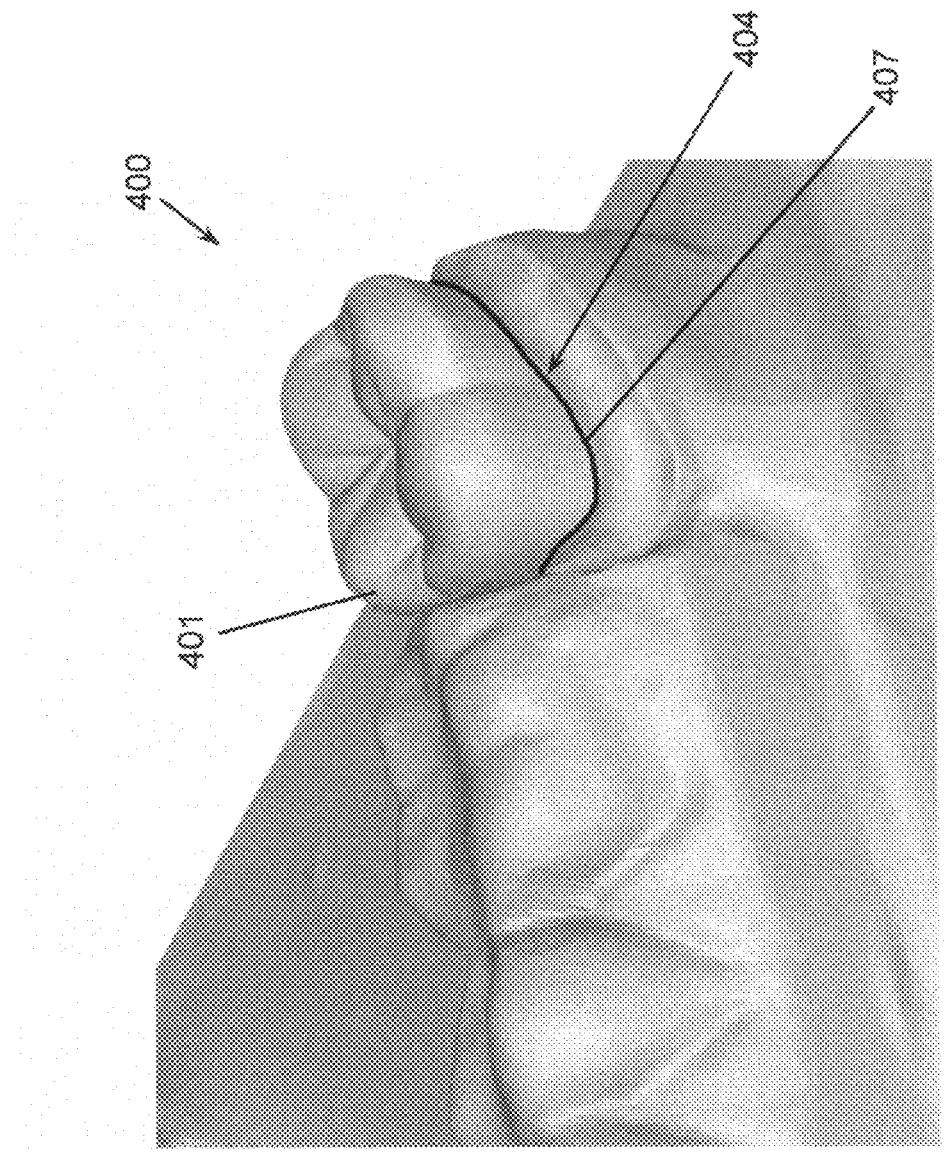
FIG. 4 illustrates a perspective view of an electronic model representing a restoration having a crown component and a coping substructure according to one embodiment of the disclosure.

FIG. 4 illustrates an electronic model representing a restoration 400 having a crown 401 and a coping substructure (not shown) according to one embodiment of the present disclosure. The restoration 400 is installed onto an abutment 404 (best seen in FIG. 2, reference no. 204) such that the bottom edge of the restoration 400, as defined by the bottom edge of the coping substructure, mates with the margin curve 407 of the abutment 404. The coping structure is not visible because it occupies the space between the crown 401 and the abutment 404. Using polygonal mesh-based electronic models to represent the crown 401 and the coping substructure enables a user to control and manipulate the interaction of these components before the restoration 400 is fabricated. Consequently problems that may arise during interaction may be eliminated before a significant amount of fabrication material or labor is expended. Furthermore, all components of the dental restoration 400 may be specified as to shape, size, and orientation to form complementary surfaces.

Figure 5:
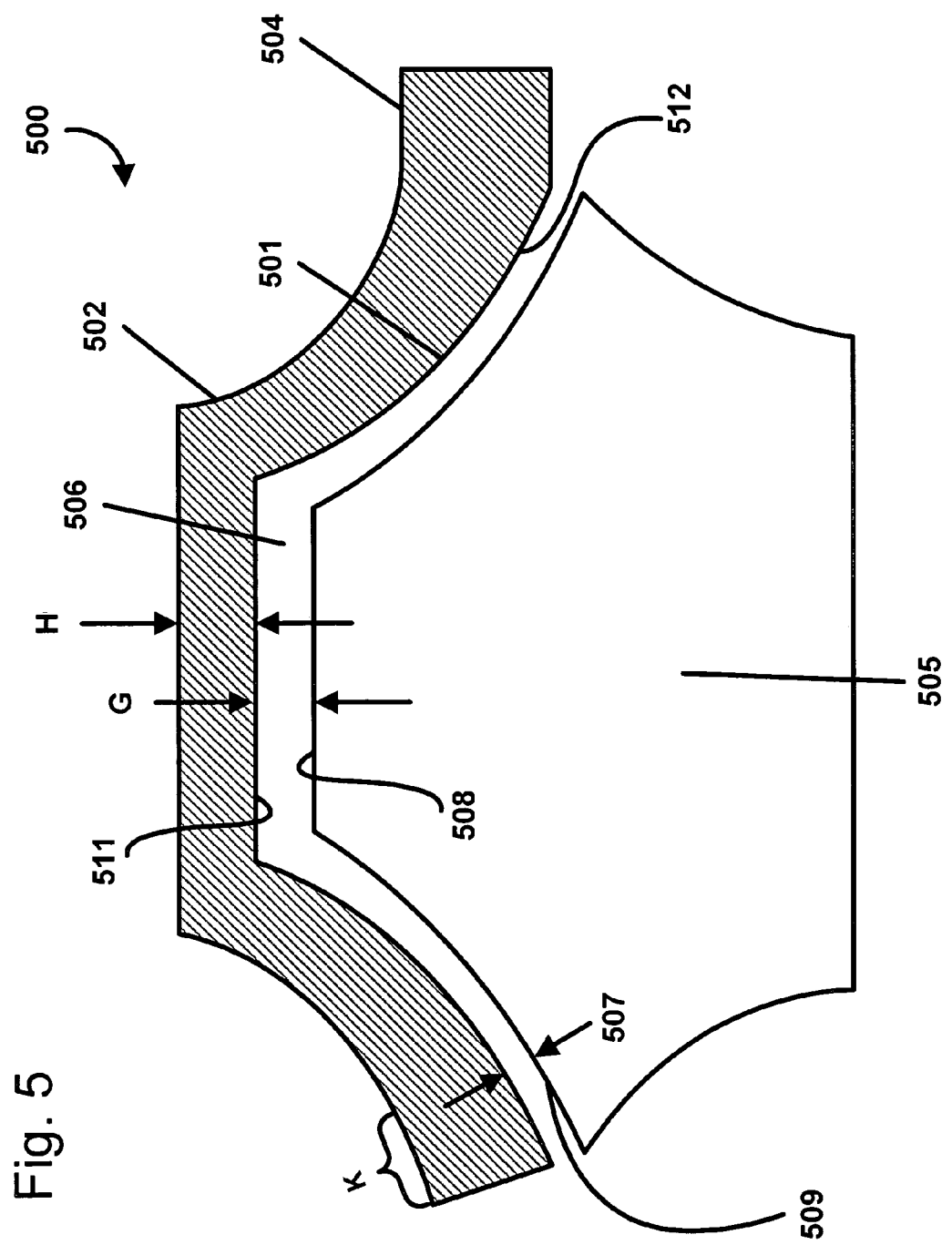
FIG. 5 illustrates a cross-sectional view of a schematic electronic model of a coping substructure designed to be installed between an abutment and a crown component in accordance with one embodiment of disclosure.
Figure 6:
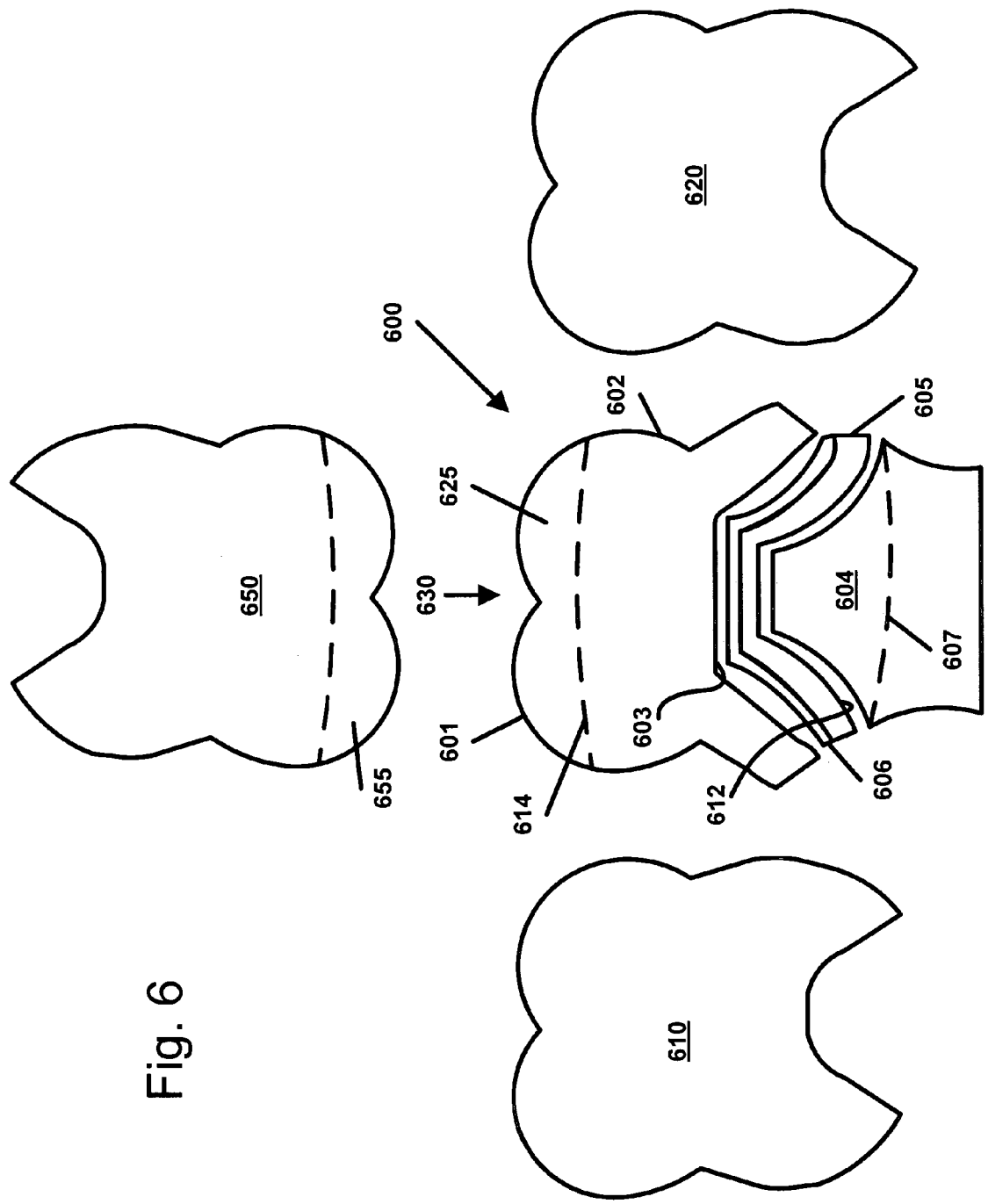
FIG. 6 illustrates a schematic of a restoration, coping and opaque layer mounted onto an abutment in accordance with one embodiment of the disclosure.

FIG. 5 illustrates a cross-section of a polygonal mesh electronic model of a coping substructure 500 designed to be installed between an abutment 505 and a restoration (as shown in FIG. 6). An offset mesh 501 and an exterior mesh 502 are designed, merged, printed, and cast to form the coping structure 500. Generally, the coping substructure 500 is cast from a metal and the crown component is pressed from a ceramic. However, the invention is not so limited. Non-limiting examples of fabrication materials for coping substructures and crown components include metals, ceramic, plastic, resins, and any other suitable material.

The coping offset mesh 501 is designed to mate with the abutment 505. In particular, the offset mesh 501 is designed to create a cement gap 506 having a width G between an upper surface 508 of the abutment 505 and a central portion 511 of the offset mesh 501. The cement gap 506 generally ranges between 0.05 mm to 0.1 mm. In some embodiments, the offset mesh 501 is further designed to leave a margin offset 507 between the surface 509 along the perimeter of the abutment 505 and a margin seal 512 along the perimeter of the offset mesh 501. The margin seal generally extends over a distance K of 1 mm inward from the margin curve. In general, the margin offset ranges between 0 and 0.1 mm. Typically, the margin offset ranges from 0 to 0.02 mm. In a preferred embodiment, the margin offset is 0 mm.

The exterior mesh 502 is designed so as to create a coping substructure 500 having a thickness H. According to one embodiment, the exterior mesh 502 of the coping substructure 500 is designed based on the shape and boundaries of the offset mesh 501 (i.e., the margin curve). According to another embodiment, the exterior mesh 502 is designed to mate with the inner surface of a restoration as shown in FIG. 6, reference no. 600. According to yet another embodiment, the exterior mesh 502 is designed based on a coping model obtained from a library of dental models. In one embodiment the shape and orientation of the exterior mesh 502 and of the offset mesh 501 of the coping substructure 500 are manipulated using graphical manipulation software. According to another embodiment, graphical manipulation software is used to deform select portions of one or both meshes 501, 502.

In some embodiments, the exterior mesh 502 includes a collar 504 for further supporting the crown component to be installed on the coping 500. The collar 504 is formed when the exterior mesh 502 extends outward past the offset mesh 501. According to one embodiment, the collar 504 encircles the entire coping 500. According to another embodiment, the collar 504 only partially encircles the coping 500. Typically, this partial collar 504 extends outward on the lingual side of the coping 500 and recesses on the facial side of the coping 500 so that the collar 504 and coping 500 are not visible on the facial side of the restoration.

FIG. 6 illustrates a schematic view of a restoration 600 and corresponding abutment 604 in accordance with one embodiment of the present disclosure. The restoration 600 is shown relative to adjacent teeth 610, 620 and antagonistic tooth 650. The restoration 600 includes a crown 625 and a coping substructure 605. The crown 625 includes a crown top 601 forming an occlusal surface, crown sides 602 forming axial walls, and an offset mesh 603 forming a complementary surface for the coping substructure 605. The abutment 604 has a perimeter, which is often referred to as the margin curve 607. This margin curve 607 defines the boundary of the bottom surface of the restoration 600.

The crown top 601 includes an occlusal surface designed to mate with the surface 655 of the antagonistic tooth 650. Typically, the crown top 601 is selected from a library of dental models stored within a computer-based dental modeling system. This library includes models that represent surfaces of various human teeth. Some of these models include molars, pre-molars, incisors, and portions thereof. The particular model chosen from the library depends upon the type of dental appliance to be created.

In a preferred embodiment, each model in this library includes an electronic polygonal mesh representation that has been scanned using a process similar to the one described above to generate the electronic models of the maxillary dentition 203 and mandibular dentition 202 shown in FIG. 2. Of course, any such library of model meshes may be utilized without deviating from the spirit and scope of the present invention. In an alternate embodiment, electronic model meshes are created from pre-existing physical libraries of restorations and other dental appliances. In yet another embodiment, the library models are developed independently by scanning individual restorations and other dental appliances and/or study casts created by dental labs. In still yet another embodiment, the crown top 601 is designed based on the occlusal surfaces of the surrounding teeth.

Once a crown top 601 is selected, sized, and positioned appropriately, crown sides 602 are constructed to define the outer shape of the crown 625. The dotted line 614 represents the area where the crown sides 602 intersect the crown top 601. In particular, the crown sides 602 are designed to connect the crown top 601 to the margin curve 607, thereby forming axial walls without interfering with adjacent teeth 610, 620. Example methods for forming the crown sides 602 will be discussed in further detail herein. In one embodiment, crown sides 602 include a single polygonal mesh. In another embodiment, crown sides 602 include multiple polygonal meshes.

A crown offset surface 603, which is also represented by a polygonal mesh, corresponds to the inner surface of the crown 625 and is designed to provide a mating surface between the crown 625 and the top surface contours of the abutment 604 or the coping substructure 605. In an alternative embodiment, the crown offset surface 603 forms the mating surface with an opaque layer 606 covering the coping substructure 605. The area between the crown top 601, crown side 602, and the crown offset mesh 603 represents the region of space to be filled by a dental material, such as gold or ceramic, during fabrication of the crown 625.

The crown offset mesh 603 is checked to identify and eliminate any undercut shapes that would prevent the insertion of the crown 625 onto to the coping substructure 605 along a path of an insertion vector 630. Likewise the inner surface 612 of the coping substructure 605 is checked against the surface of the abutment 604. Typically the cement gap, which is best seen in FIG. 5, reference no. 506, is defined by the space remaining after the elimination of this undercut volume.

According to one embodiment, the crown top 601 polygonal mesh, crown side 602 polygonal mesh, and the crown offset 603 polygonal mesh are converted into an electronic specification (e.g., an STL file) that is used to print a wax model of the crown 625 using rapid prototyping processes. This wax model can be used to press the crown 625 using a lost wax processing technique. This approach enables the crown 625 to be fabricated from a first dental material such as ceramic. The polygonal mesh representing the coping substructure 605 may also be translated into an electronic specification, printed, and cast as described herein. In one embodiment the coping substructure 605 is fabricated using a second dental material such as gold or other such metal. In some embodiments, the two fabricated components 605, 625 are pressed together to create a dental restoration 600 ready for installation on the abutment 604.

Figure 7:
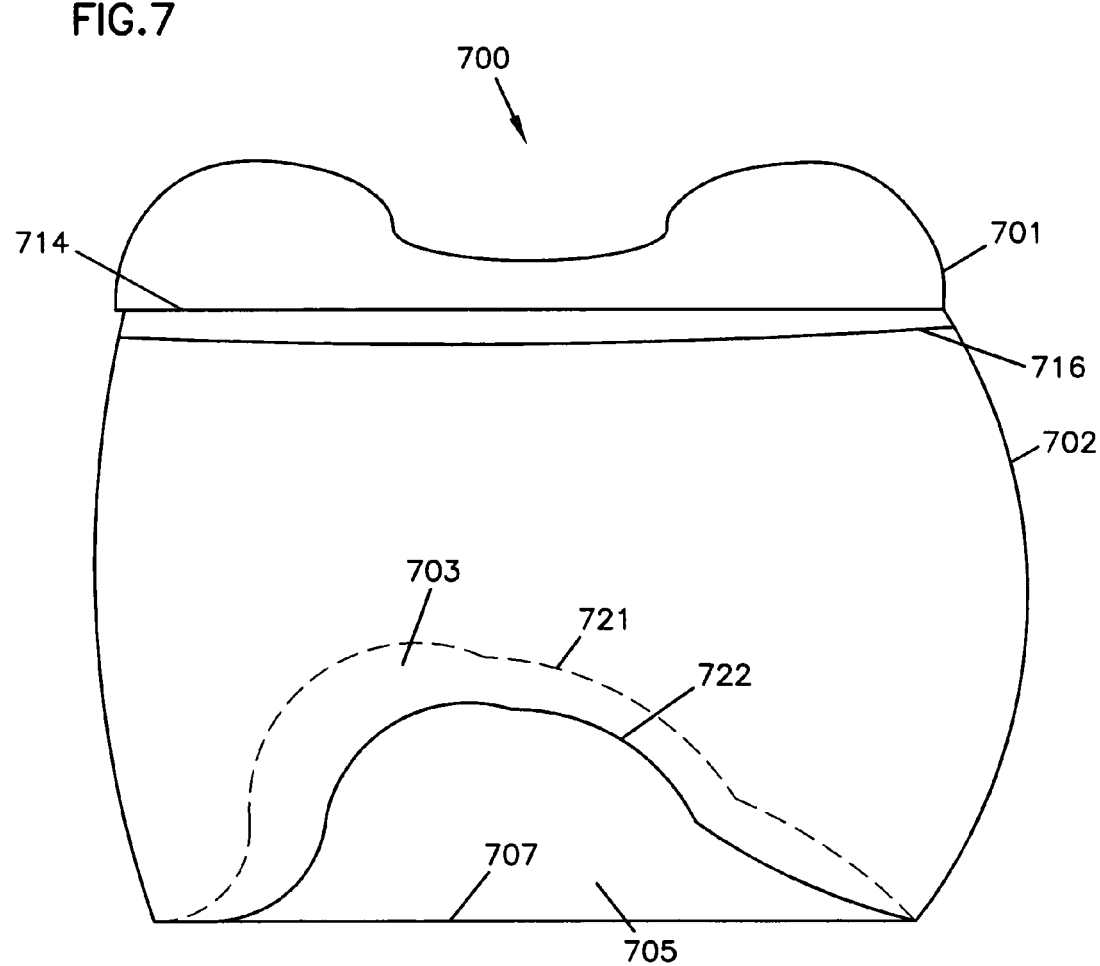
FIG. 7 illustrates the construction of a polygonal mesh based electronic model representing side surfaces of a restoration in accordance with one embodiment of the invention.

FIG. 7 illustrates the construction of polygonal mesh based electronic models representing the side surfaces of a restoration 700 in accordance with one embodiment of the disclosure. An occlusal surface 701 mesh, having a perimeter 714, is shown positioned above a margin curve 707 mesh. The electronic models representing the side surfaces 702 of the restoration 700 are generated between the occlusal surface 701 mesh and the margin curve 707 mesh. The shape of the side surfaces 702 is varied to obtain a desired shape and to avoid interference between the restoration 700 and adjacent teeth. According to one embodiment, the shape of the side surface 702 mesh is modified by displaying the side surface 702 mesh, the occlusal surface 701 mesh, and the margin curve 707 mesh on a computer display and using computer software to transform portions of the side mesh 702 to a desired position. Any type of graphical manipulation software may be used to transform the side mesh 702. Examples of graphical manipulation performed by such software include sizing, positioning, rotating, and deformation (i.e., repositioning or shaping of select points or areas).

According to another embodiment, the crown side 702 is formed based on an occlusal surface perimeter curve 714, a curve to control tangency 716, and the margin curve 707. The occlusal surface perimeter curve 714 and the margin curve 707 define the edges of the crown side 702. The amount by which the crown side 702 arcs or curves outward between the occlusal surface perimeter 714 and the margin curve 707 depends on the location and shape of the tangency curve 716. In one embodiment, the tangency curve 716 is defined by point positions initially selected by computer software. A user modifies these point positions as needed to create adequate separation from the restoration 700 and the adjacent teeth (not shown). In another embodiment, a user initially selects the point positions defining the tangency curve 716. Generally, this method is used to generate crown sides 702 for posterior restorations (e.g., molars).

According to another embodiment, the crown side 702 is formed based on the occlusal surface perimeter 714, the margin curve 707, and a series of control curves (not shown). Various embodiments of these control curves extend longitudinally between the occlusal surface perimeter 714 and the margin curve 707 and/or latitudinally around the perimeter of the restoration 700. In one embodiment, these control curves are defined based on similar curves from adjacent teeth. In another embodiment, these control curves are defined based on curves found on models from a library similar to the model library discussed above. Each of the curves can be transformed and manipulated by a user or by computer software to create an asymmetrical or non-cylindrical restoration. Generally, this method is used to generate side surfaces 702 for anterior restorations.

Figure 8:
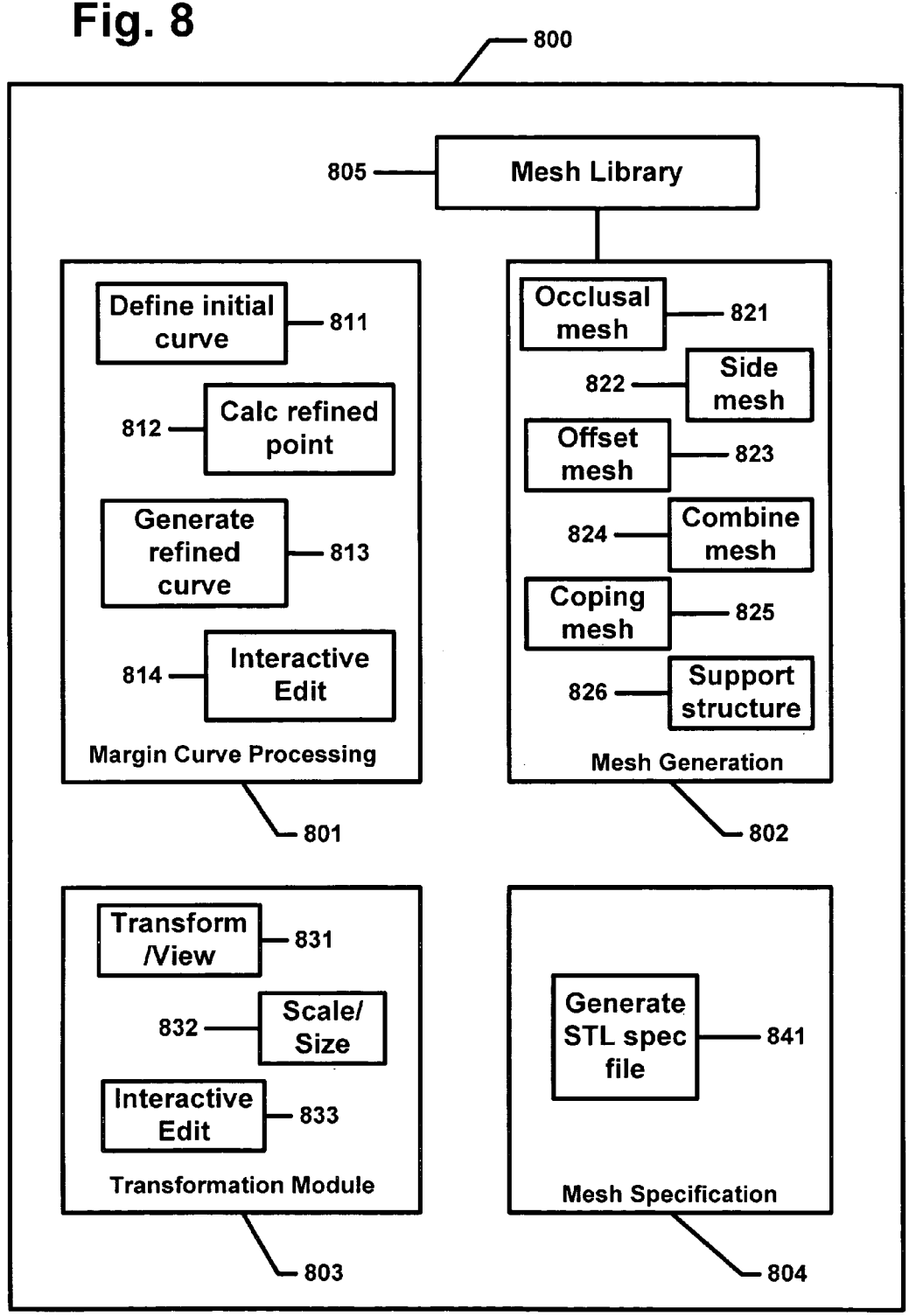
FIG. 8 illustrates a set of processing modules within a processing system utilized to implement a method for creating dental appliances from electronic models in accordance with one embodiment of the disclosure.

FIG. 8 illustrates a set of processing modules within a processing system 800 utilized to implement a method for creating dental appliances from electronic models using lost-wax manufacturing processes. The processing system 800 is constructed using a margin curve processing module 801, a mesh generation module 802, a transformation module 803, a mesh specification module 804, and a mesh library 805. These modules 801-805 implement the electronic modeling processes described herein. For example, in one embodiment, these modules 801-805 implement electronic modeling of restorations.

The margin curve processing module 801 performs the processing associated with the definition and use of a margin curve of an abutment. The margin curve defines the boundary of the offset mesh of a coping or restoration. Generally, the margin curve follows the perimeter of the gingival surface of the abutment. The margin curve processing module 801 includes a define initial curve module 811, a calc refined point module 812, and a generate refined curve module 813.

The define initial curve module 811 defines an initial margin curve around an abutment. In one embodiment, a user manually chooses one or more initial points on the margin curve. Computer software is used to draw a curve through these points. In another embodiment, computer software chooses the initial points on the margin curve.

The calc refined point module 812 is used to select refined margin points to create a smoother, more useable margin curve. In one embodiment, the computer software determines an apex point (i.e. a point of maximum curvature furthest from the center of the abutment) in the same longitude as the initial margin point. The generate refined curve module 813 generates a modified margin curve by translating each of the points along the initial margin curve to the refined margin points.

The margin curve processing module 801 further includes an interactive editing module 814. The interactive editing module 814 is used to interactively transform either the modified or the initial margin curve. In one embodiment, a section of the refined margin curve is deformed to extend to a different area of the abutment. For example, the refined margin curve of a coping may be deformed away from the Gingiva so that the coping will not be visible near the gingival surface of the abutment.

The mesh generation module 802 and the mesh library 805 are used to generate a mesh that represents the dental appliance. For example, the mesh generation module 802 can be used to generate electronic models representing the crown components and the coping substructure of a restoration as discussed above. The mesh generation module 802 includes an occlusal mesh module 821, a side mesh module 822, an offset mesh module 823, a combine mesh module 824, and a coping mesh module 825. In one embodiment, the mesh generation module 802 further includes a support structure mesh module 826.

The occlusal mesh module 821 generates an occlusal mesh using pre-defined library meshes that are obtained from the mesh library 805. The side mesh module 822 generates a side mesh surface extending from the perimeter of the occlusal mesh to the refined margin curve. The offset mesh module 823 generates an offset mesh based on the surface of the abutment or coping substructure. The offset mesh is generated so as to provide an offset space needed to install the appliance onto the abutment. The combine mesh module 824 stitches the occlusal, side, and offset meshes together into a combined crown mesh. The coping module 825 generates a coping mesh representing the coping substructure separate from the crown components. The support structure module 826 generates a support structure mesh, which will be described in more detail herein.

The transformation module 803 permits an operator to manipulate and view various meshes on a computer display device. In one embodiment, this module 803 includes a position and view module 831 to position and orient occlusal, side, offset, coping, and other such meshes on a display relative to each other. In another embodiment, this module 803 further includes a scale and size module 832 to modify the size and dimensions of each mesh during the manipulation process. In yet another embodiment, this module 803 includes an interactive transformation module 833 for interactively deforming sections of each mesh. In one embodiment, the separate occlusal, side, and offset meshes are modified before being combined in the combined mesh module 825. In another embodiment, the meshes are combined into a restoration mesh and then modified in the restoration transformation module 803.

The mesh output module 804 contains a generate STL spec file module 841 for converting the crown, coping, and support structure meshes into a format readable by a rapid prototyping machine. In particular, the meshes are converted into a Stereo lithography (STL) file. As discussed above, the rapid prototyping machine generates a wax impression based on the STL file. The wax impression is usable in a lost-wax fabrication process to manufacture the dental appliance.

While the above description applies mainly to restorations, the invention is not so limited. Applicants note that various embodiments of these processing modules 801-805 are used to model and fabricate other dental components. Examples of other such dental components include bridge frameworks, implant posts, tooth substitutes, and the like.

Referring now to FIGS. 9 and 10A-10H, the principles of the present invention are utilized to create a two-piece restoration 1000. FIG. 9 illustrates an operational flow chart depicting steps for modeling and fabricating the restoration 1000 and FIGS. 10A-10H illustrate these steps. In this example, a porcelain fused to metal (or PFM) restoration 1000 is created. The example is identified generally at 900 and starts at block 902. The example first proceeds to block 903 where an abutment 1009 having a margin curve 1013 is scanned. According to one embodiment, the scan is performed by a scanner, as shown in FIG. 3, reference no. 354, with the resulting scan data being provided to the computer system 300. In the preferred embodiment, a study cast taken from one or more dental impressions is scanned rather than the actual abutment 1009. However, other direct and indirect scanning methods may be employed without deviating from the spirit and scope of the invention.

Figure 10A:
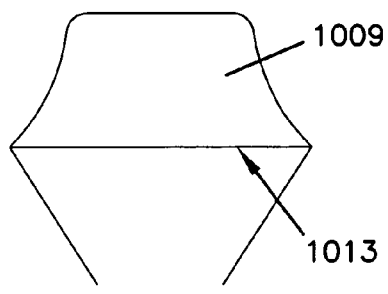
FIGS. 10A-10H illustrate the steps included in FIG. 9.
Figure 10B:
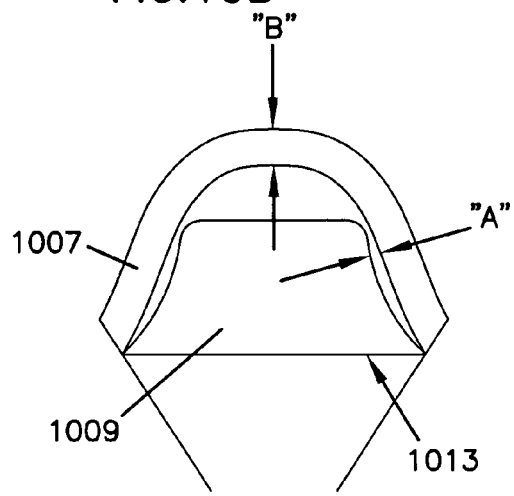
Figure 10C:
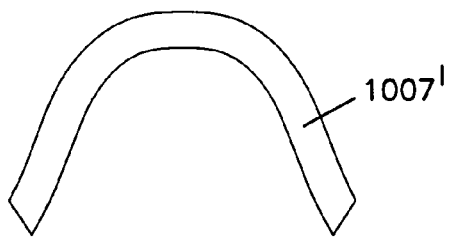

After scanning, the scanned data is used to create a coping substructure 1007 at block 904. The coping substructure 1007 is generally designed to abut the margin curve 1013 in an appropriate manner as will be discussed in greater detail herein. The resulting coping substructure 1007 is shown in FIG. 10C. It will be appreciated that at this stage the coping substructure 1007 is a virtual structure.

Figure 10D:
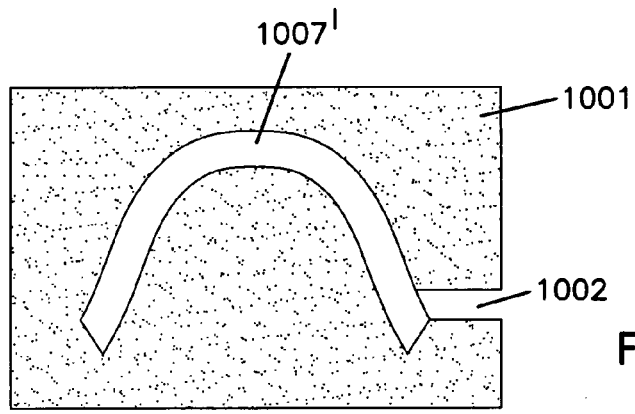

At block 906, an STL file for the designed coping substructure 1007 is generated by the computer system 300 and output to a rapid prototype machine. The machine prints out a physical wax version 1007' of the coping substructure 1007 designed at block 904. Moving to block 908, the coping substructure 1007' is cast using a lost wax technique. FIG. 10D illustrates the casting process with the physical wax version 1007' placed into the investment material 1001 with sprue 1002.

Figure 10E:
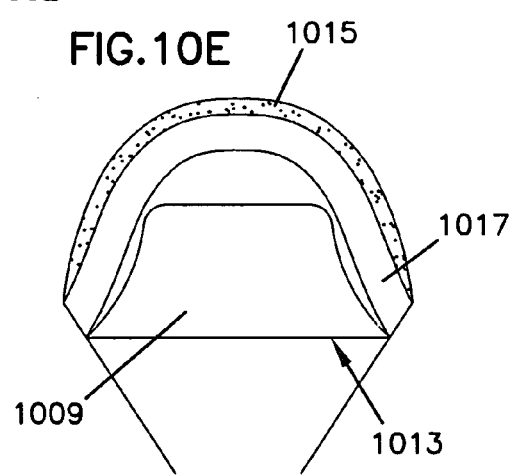
Figure 10F:
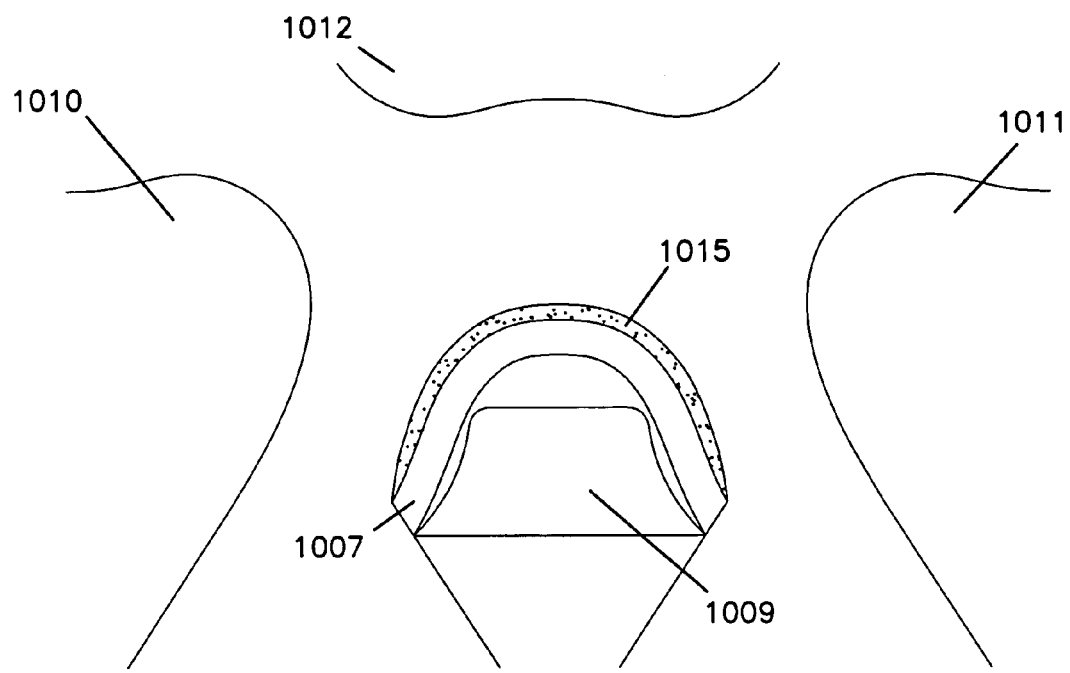

After casting, the method moves to block 910 where the resulting cast coping substructure 1017 may optionally have an opaque layer 1015 placed on it. In various embodiments the opaque layer 1015 is painted by hand, manually or automatically sprayed, and manually or automatically dipped onto the coping substructure 1017. FIG. 10E illustrates the coping substructure 1017 with an opaque layer 1015 covering the abutment 1009, while FIG. 10F illustrates the combined coping substructure 1017 and opaque layer 1015 on the abutment 1009 portion of the physical study cast. Adjacent teeth 1010, 1011, and antagonistic tooth 1012 are also illustrated in FIG. 10F.

At block 912, the physical study cast is preferably scanned again with the combined coping substructure 1017 and the opaque layer 1015 in place on the abutment 1009. After scanning, the crown portion 1005 of the restoration 1000 is designed at block 914 as discussed herein. An electronic model of the crown portion 1005 is superimposed over the electronic model of the coping substructure 1007 and opaque layer 1015.

Figure 10G:
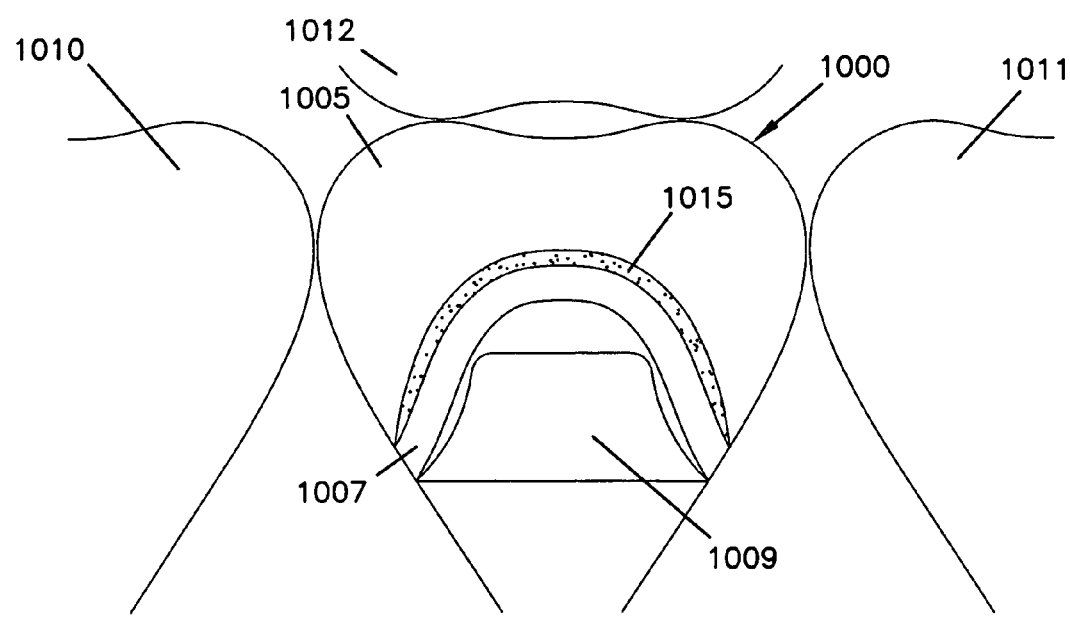

FIG. 10G illustrates the electronic model of the two-piece PFM restoration 1000 including the coping substructure 1007, the opaque layer 1015, and the crown portion 1005 surrounded by adjacent teeth 1010, 1011. The electronic model of the restoration 1000 can be transformed, scaled, oriented, and deformed to fit with the adjacent teeth 1010, 1011. At block 916, an STL file for the crown portion 1005 is created and is output to a rapid prototyping machine (not shown). A wax print 1025 of the crown portion 1005 is then created.

Figure 10H:
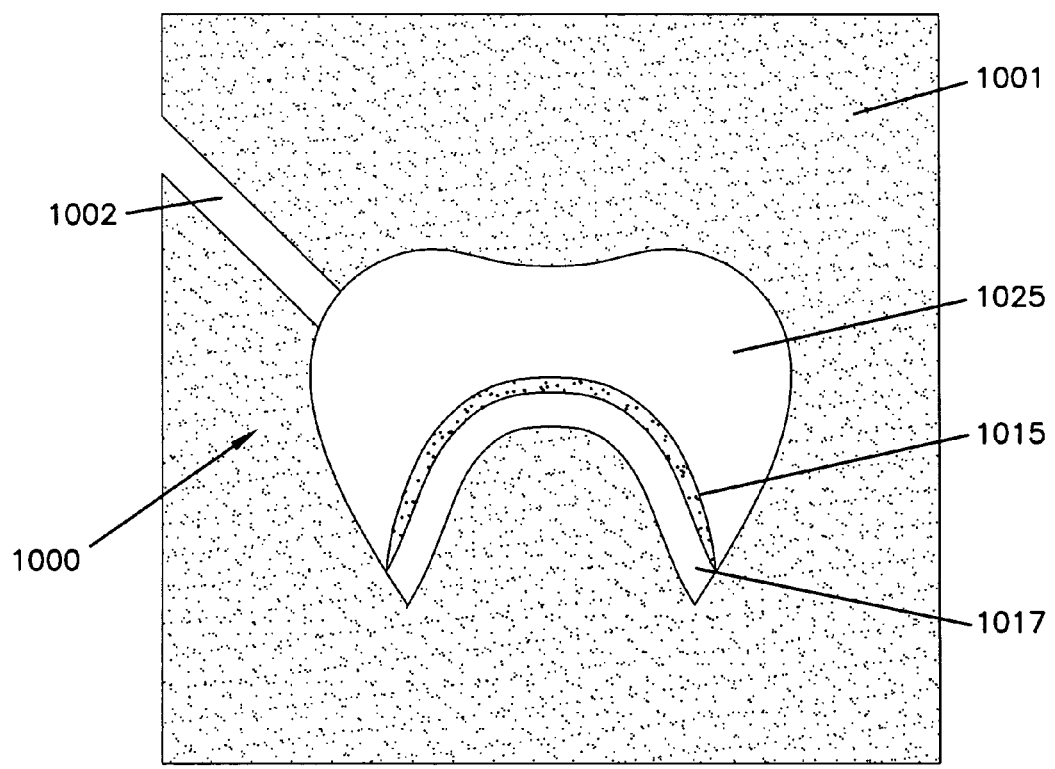

At block 918, the wax print 1025 of the crown portion 1005 is pressed onto the combination coping substructure 1017 and opaque layer 1015. FIG. 10H illustrates the combination placed in the investment 1001 with sprue 1002. The wax is burned out and ceramic or other such dental material is pressed in through the sprue. The resulting two-piece restoration (with coping substructure) can then be cleaned and readied for use in the patient's mouth.

Applicants note that lost-wax fabrication is only one exemplary means of dental appliance fabrication. In another embodiment, an electronic model of a coping or crown may be rapid prototyped directly. For example, a metal coping could be prototyped using direct metal printing using a process such as ProMetal® 3D printing used by Ex One. A restoration or portions thereof could also be printed directly from ceramic, plastic, metal, or other such material.

Figure 11:
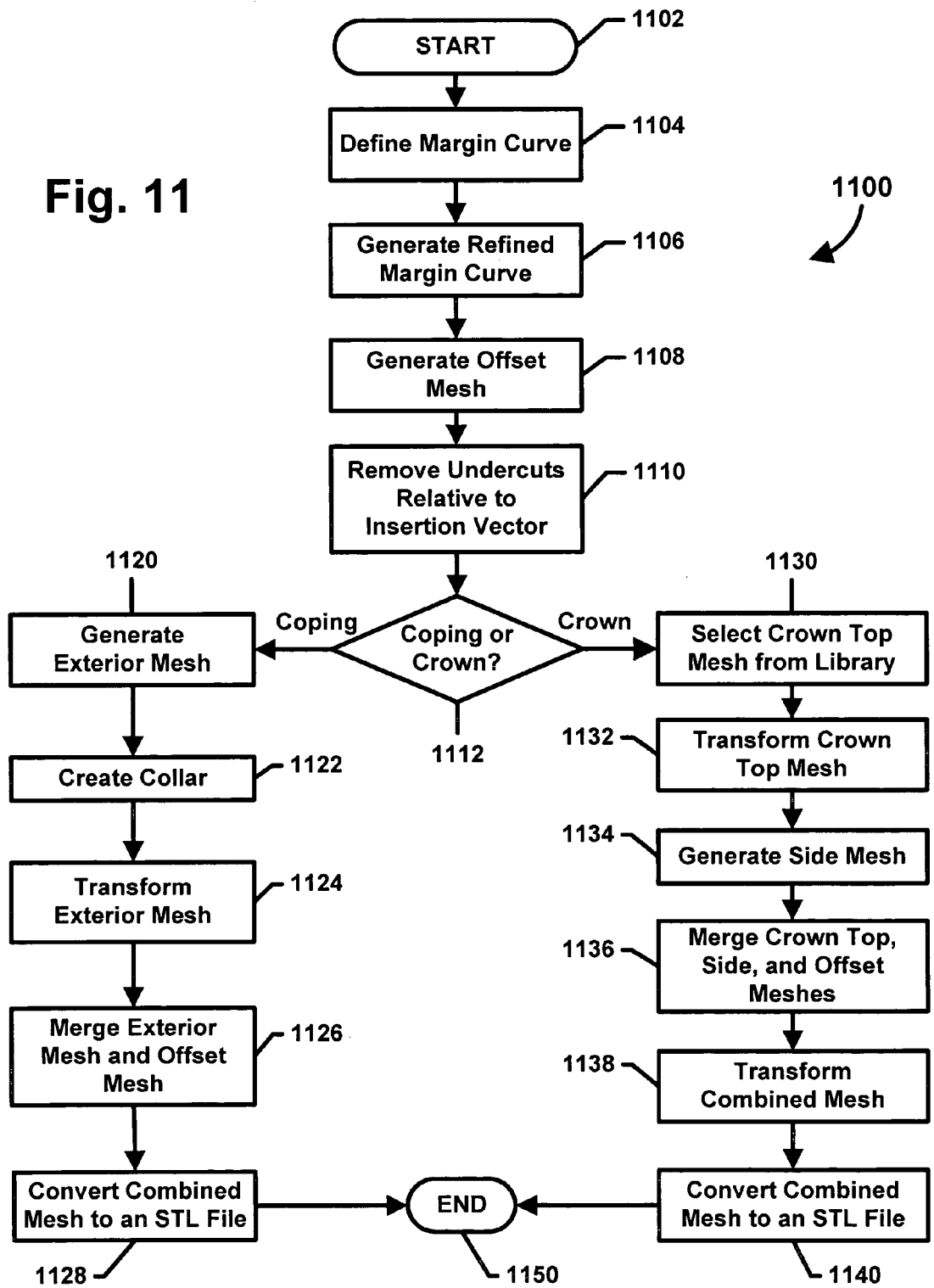
FIG. 11 illustrates an operational flow for designing the crown portion and coping substructure of a restoration in accordance with one embodiment of the disclosure.

FIG. 11 illustrates an operational flow for an example method for designing the crown portions and coping substructures of a restoration. These processes describe modules 904 and 914 from FIG. 9 in more detail. The processing is generally identified at 1100, and begins at 1102. The processing then proceeds to module 1104 to define a margin curve. The define margin curve module 1104 generates a definition for the margin curve around the abutment of an electronic model representing a patient's dentition. As discussed above, this curve is used to define the dental restoration's interface surface with the abutment.

The margin curve is processed in module 1106 to generate the refined margin curve. This refined margin curve provides a more accurate definition for the bottom surface of the restoration while permitting the proper generation of an offset space between the abutment and the offset mesh. The offset mesh is generated in module 1108. The offset mesh provides a mating surface to the abutment with allowance for offset space. This offset space may be a uniform distance of a predetermined value or may be a varying distance depending upon the location over the abutment.

In a preferred embodiment, the offset spacing is shown to a dental professional using a color mapping mechanism that illustrates a distance between the inner and outer surfaces using a set of colors. The colors, each of which corresponds with a particular range of distances, are superimposed on the electronic model of the offset mesh. However, the invention is not limited to using color to depict offset distance and any suitable means to depict offset distance may be used. The processing then continues to module 1110 where undercuts in the offset mesh are removed relative to an insertion vector along which the dental appliance will be installed on the abutment.

The process 1100 flows through modules 1102-1110 whether a crown portion or a coping substructure portion is being designed. However, the process splits at module 1112 depending on which portion is being created. Module 904 of FIG. 9 would proceed to module 1120. Module 914 of FIG. 9 would proceed to module 1130.

Proceeding now to module 1120, the exterior mesh of a coping substructure is generated. In one embodiment, the exterior mesh is generated at least in part based on the offset mesh. In another embodiment, the exterior mesh is generated at least in part based on a model mesh from a library of model meshes. In module 1122, the collar style of the coping substructure is designed. For example, in varying embodiments, the collar style is feathered and/or is designed to accommodate chamfer, shoulders, and feather style abutments. In one embodiment, the collar fully encircles the coping substructure. In another embodiment, the collar only partially extends around the coping substructure. In some embodiments, generating the exterior mesh includes designing the collar.

The exterior mesh is then transformed to a desired shape, size, and position in module 1124. For example, in some embodiments the exterior mesh is smoothed out to allow a better fit with the offset mesh of a crown. In other embodiments, bumps or other deformities are added to the exterior mesh to provide a firmer attachment between the coping substructure and the crown portion. The exterior mesh and the interior mesh are then merged into a coping substructure mesh in module 1126 and converted to an STL mesh and fabricated in module 1128. The process ends at 1150.

In the alternative, when creating a crown portion, the process 1100 proceeds from the module 1112 to the module 1130. In module 1130, a normalized crown top mesh is selected from a library of mesh specifications. The crown top mesh is then transformed in module 1132. Transformation of the mesh includes the selection of crown top scaling match points for scaling the normalized crown top mesh to the size needed for a given patient. The crown top mesh is also placed above the abutment, positioned, and oriented so as not to interfere with adjacent and antagonistic teeth. In one embodiment, the module 1132 also simulates the interaction of the crown top mesh with antagonistic teeth, thereby enabling a determination of the optimal placement and orientation of the crown top mesh.

Next, the side mesh surfaces are generated between the perimeter of the crown top mesh and the refined margin curve in module 1134. This process attempts to define a smooth, curved surface. The crown top mesh, the side mesh, and the offset mesh are merged together in module 1136 to create a combined electronic model for a solid object representing the dental appliance.

In module 1138, the shape, size, and orientation of the dental appliance may be further transformed as discussed above. Similar modifications, if desired, may be made to all or part of the crown top mesh, the offset mesh, or the side mesh individually to create an aesthetically pleasing shape and to correct the interaction of the crown top surface with the adjacent and antagonistic teeth. For example, in one embodiment, the restoration is deliberately undersized to enable the outer surface to be created from Feldspathic ceramic one layer at a time.

Once the combined mesh for the dental appliance is complete, module 1140 generates an output file containing the dental appliance specification in an STL format. The process ends 1150.

Bridges and Implants

Figure 12:
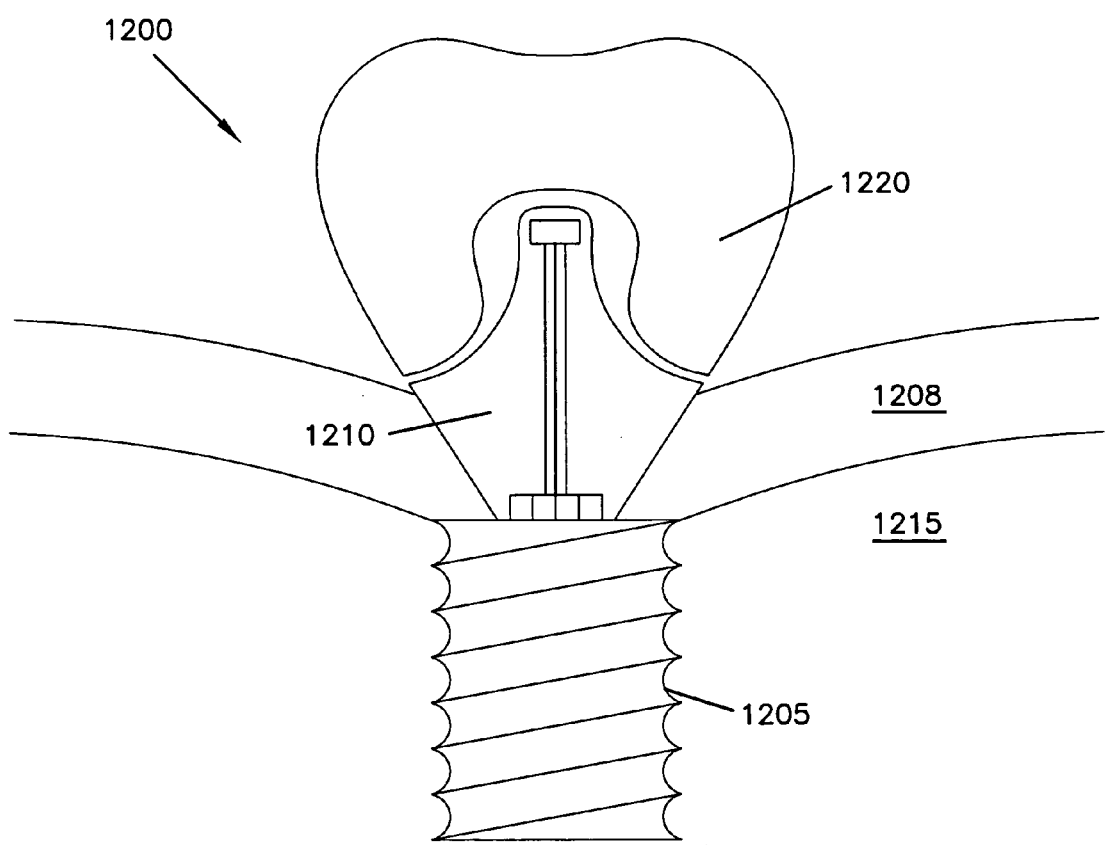
FIG. 12 illustrates an example of an electronic model of a dental implant according to one embodiment of the disclosure.
Figure 13:
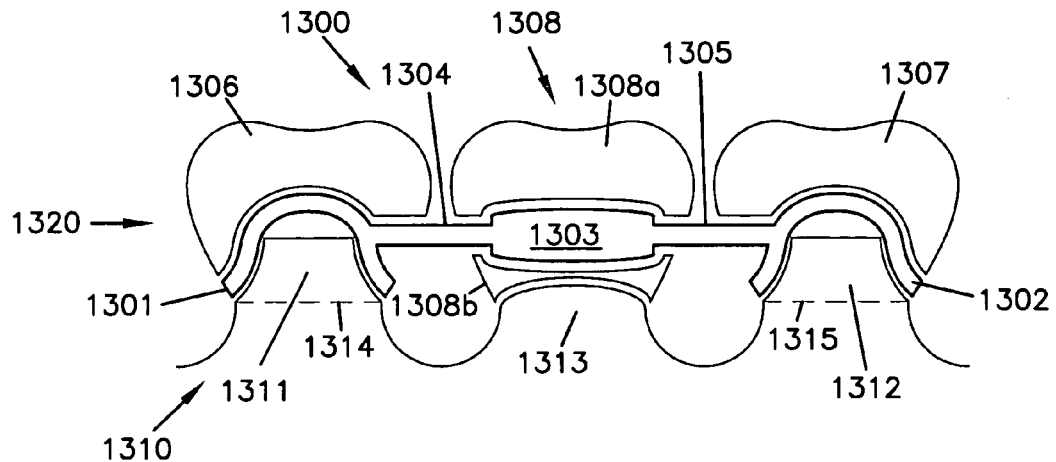
FIG. 13 illustrates a cross-sectional view of an example electronic model of a dental bridge according to one embodiment of the disclosure.
Figure 14:
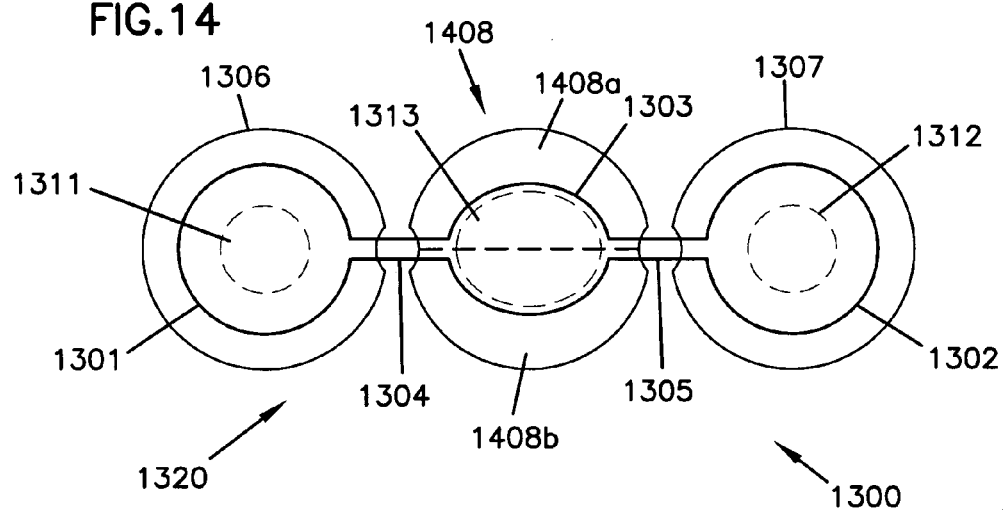
FIG. 14 illustrates a top-down view of the electronic model of FIG. 13.

Referring now to FIGS. 12-14, the techniques of fabricating an electronic model of a restoration as described above can be applied to the construction of dental implants, bridges, and other dental appliances as well. FIG. 12 illustrates an example of an electronic model 1200 of a dental implant according to one embodiment of the disclosure and FIGS. 13 and 14 illustrate an example electronic model 1320 of a dental bridge 1300.

Referring now to FIG. 12, an electronic model of a dental implant 1200 includes a post 1205 for mounting to the alveolar bone 1215 of a patient, a tooth substitute 1210 mounted to the post 1205 and extending through the Gingiva 1208 of the patient, and a crown 1220 mounted to the tooth substitute 1210. The post 1205 functions as an anchor holding the tooth substitute and crown in place. In one embodiment, the tooth substitute 1210 functions as an abutment onto which the crown 1220 is installed. In another embodiment, a coping substructure or a bridge framework is installed on the tooth substitute 1210. According to one embodiment, only the crown 1220 is electronically modeled and rapid prototyped. According to another embodiment, the crown 1220 and the tooth substitute 1210 are electronically designed to fit together and then sequentially rapid prototyped and fabricated. In some embodiments, the process for electronically modeling, printing, and fabricating the tooth substitutes 1210 is substantially similar to the crown and coping fabrication processes described herein.

Referring now to FIG. 13, a cross-sectional view of an example of an electronic model 1320 of a dental bridge 1300 is illustrated superimposed over an electronic model 1310 of a patient's dentition. The electronic model 1310 of the dentition includes a first and second abutment 1311, 1312 and a pontic site 1313, which is a location that would otherwise be occupied by an abutment. The electronic model 1320 of the bridge 1300 includes a first and second coping 1301, 1302 mounted onto the abutments 1311, 1312 of the electronic model 1310. Dental crowns 1306, 1307, and 1308 are shown mounted on top of the copings 1301, 1302 and the pontic 1303, respectively.

The electronic model 1320 further includes a pontic 1303, which functions as an abutment 1311, 1312, coupled between the first and second copings 1301, 1302 over the pontic site 1313. In an alternative embodiment that does not utilize coping substructures, the pontic 1303 is coupled between the first and second crowns 1306, 1307. The pontic 1303 is typically formed of metal, but can be formed of any desired material. In another embodiment (not shown), a dental bridge 1300 includes two or more consecutive pontics between the two copings 1301, 1302. In yet another embodiment (not shown), a dental bridge includes two pontics and a first, second, and third coping. In one example of this embodiment, the first pontic is coupled between the first and second copings and the second pontic is coupled between the second and third copings.

Referring still to FIG. 13, the pontic 1303 is coupled between the first and the second coping 1301, 1302 by a first and a second connector 1304, 1305, respectively. Typically, the connectors 1304, 1305 and copings 1301, 1302, 1303 are electronically modeled, printed, and cast or pressed as a unitary piece. In an alternative embodiment, the cast connectors 1304, 1305 couple to the pontic 1303 and the copings 1301, 1302 through welding, adhesive, or other such attachment means.

The two copings 1301, 1302 have been fitted with dental crowns 1306, 1307, which are similar to the dental crowns described above with reference to FIGS. 6 and 7. The dental crowns 1306, 1307 are arranged and configured to enable the connectors 1304, 1305 to extend from the copings 1301, 1302, respectively, to the pontic 1303. A third dental crown 1308 is designed to install onto the pontic 1303. According to one embodiment, the crowns 1306-1308 are fabricated by printing wax shells of the three dental crowns 1306, 1307, 1308 and mounting the crowns 1306-1308 onto the cast copings 1301, 1302 and pontic 1303. The wax shells, copings 1301, 1302, and pontic 1303 are then placed in investment, heated, and pressed.

According to another embodiment, the wax shell of the dental crown 1308 includes a first and second section 1308a, 1308b that are pressed as a unitary piece. According to yet another embodiment, the first and second sections 1308a, 1308b are pressed separately and fastened together by adhesive, welding, or other such means. According to still yet another embodiment, the first shell 1308a is invested and pressed onto the crown 1308 first and then the second shell 1308b is invested and pressed onto the crown 1308. In one embodiment, the first piece 1308a includes an occlusal section and the second piece 1308b includes a gingival section as shown in FIG. 13.

Referring now to FIG. 14, another embodiment of a third crown 1408 configured to mount onto the pontic 1303 of the bridge 1300 includes a labial section 1408a, and a lingual section 1408b. FIG. 14 illustrates a top down view of the electronic model of FIG. 13. The dental crown 1408 is shown installed on the pontic 1303 of the bridge 1300. In yet another embodiment (not shown), the dental crown 1408 is formed from a single piece of material and has a first and second recess arranged and configured to allow the connectors 1304, 1305 to extend between the pontic 1303 and the copings 1301, 1302.

Referring now to FIGS. 13 and 14, the fabrication techniques described herein can be applied to all or some of the components of a bridge. According to one embodiment, the copings 1301, 1302 and pontic 1303 are designed by hand and only the dental crowns 1306, 1307, 1308 are electronically modeled and then constructed using the rapid prototyping and lost wax techniques described above. According to another embodiment, both the copings 1301, 1302, the pontic 1303, and the two connectors 1304, 1305 are electronically modeled to fit together and then individually constructed. Each of the components are then fastened or assembled by hand. According to yet another embodiment, the framework, which includes the first and second copings 1301, 1302, the pontic 1303, and the connectors 1304, 1305 are electronically modeled and constructed as a single, unitary piece of material.

Figure 15:
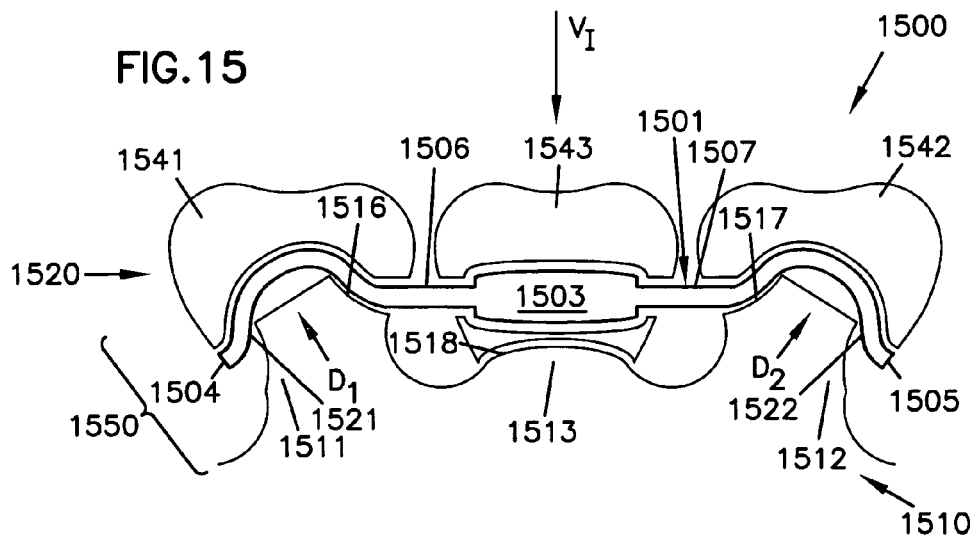
FIG. 15 illustrates an example electronic model of a bridge framework and the corresponding crown components superimposed over an electronic model of a patient's dentition.

Referring now to FIG. 15, an electronic model 1520 of a framework 1501 of a bridge 1500 is illustrated superimposed over the electronic model 1510 of a patient's dentition. The framework 1501 includes a pontic 1503 fastened between a first and second coping 1504, 1505. The electronic model 1510 of the dentition includes a first and second abutment 1511, 1512 and a pontic site 1513. The first abutment 1511 on the electronic model 1510 has an exterior surface 1516 and the second abutment 1512 has an exterior surface 1517. The pontic site 1513 has an exterior surface 1518.

Because a dental professional typically grinds down the abutments 1511, 1512 by hand, each abutment 1511, 1512 tends to have a different shape and orientation. The orientations of the first and second abutments 1511, 1512 in FIG. 15 are exaggerated to aide in illustrating this concept. The first abutment 1511 is oriented (e.g., leans or points) along a directional axis D1 and the second abutment 1512 is oriented along a directional axis D2.

In order to fit the bridge 1500 on the abutments 1511, 1512 in a manner that is both functional and cosmetically pleasing, the bridge 1500 is electronically designed to accommodate the individual orientation and shape of each abutment 1511, 1512. In particular, the bottom surfaces 1521, 1522 of the copings 1504, 1505 are designed to mate with the exterior surfaces 1516, 1517 of the abutments 1511, 1512 to enable the bridge 1500 to be installed along an insertion vector $V_I$. To fit properly, the bottom surfaces 1521, 1522 of the copings 1504, 1505 do not include any undercuts relative to the insertion vector $V_I$ (e.g., the bottom surfaces 1521, 1522 continuously extend away from the insertion vector $V_I$).

Figure 16:
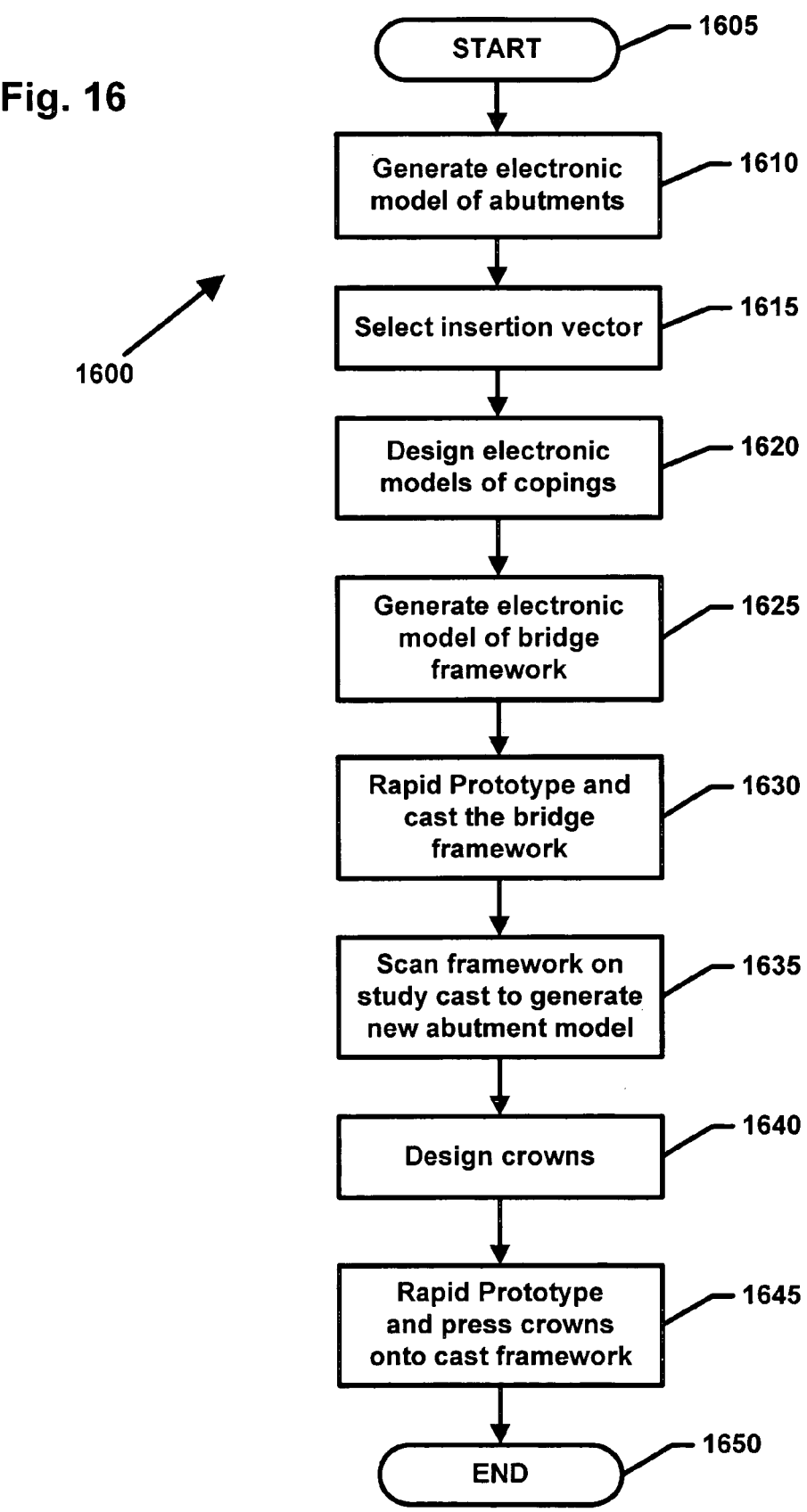
FIG. 16 illustrates an operation flow for designing a bridge according to one embodiment of the disclosure.

FIG. 16 illustrates a flow chart 1600 depicting steps for designing a bridge according to one embodiment of the present disclosure. The operations of this flowchart 1600 will be discussed with reference to the electronic models 1520, 1510 of FIG. 15. The process starts 1605 and proceeds to operation 1610, in which the electronic model 1510 representing the abutments 1511, 1512, and pontic site 1513 is generated from scanned positional data. In one embodiment, the scanned data is obtained from scanning a study cast of the patient's dentition. In another embodiment, the scanned data is obtained from a direct scan of the patient's dentition. The electronic model 1510 is displayed upon a display device like the one shown in FIG. 3, reference no. 351.

Next, in operation 1615, a user selects an insertion vector $V_I$, which is the vector indicating the path the bridge 1500 will follow when installed on the abutments 1511, 1513. In one embodiment, a user selects the insertion vector $V_I$. In another embodiment, a software program selects the insertion vector $V_I$. Once the insertion vector $V_I$ is chosen, an electronic model of each coping 1504, 1505 is generated, superimposed over the electronic model 1510 of the respective abutments 1511, 1512, and adjusted to fit the surfaces 1516, 1517 of the abutments 1511, 1512 in operation 1620. Any undercuts in relation to the insertion vector $V_I$ from the bottom surfaces 1521, 1522 of the copings 1504, 1505 are eliminated. In some embodiments, the pontic 1503 is transformed to better fit the pontic site 1513. However, the invention is not limited to this method order, which is meant to be merely illustrative. For example, the copings 1504, 1505 may be designed before an insertion vector $V_I$ is chosen and modified later based on the insertion vector $V_I$.

Operation 1625 includes generating electronic models of a pontic 1503 and connectors 1506, 1507 and merging them with the electronic models of the copings 1504, 1505. The result of operation 1625 is a framework 1501 of the bridge 1500. In operation 1630, the framework 1501 is rapid prototyped and cast using the methods described above with reference to FIGS. 9-11. The cast framework 1501' is positioned on a study cast of the abutments 1511, 1512, pontic site 1513, and surrounding dentition. The cast framework 1501' and surrounding dentition are scanned in operation 1635. A new electronic model 1550 is generated from the scanned positional data to include a new abutment for each coping 1504, 1505, and pontic 1503 scanned.

Next, electronic models of crowns 1541-1543 are generated in operation 1640. These crowns 1541-1543 are designed to install onto the framework 1501. According to one embodiment, each of these crowns 1541-1543 is designed using the techniques described with respect to FIGS. 9-11. According to another embodiment, the crowns 1541-1543 are designed using the techniques that will be described herein with reference to FIGS. 17-20. Operation 1645 includes pressing or casting each of the crowns 1541-1543 using rapid prototyping and lost wax techniques. In some embodiments, wax models of the crowns 1541-1543 are printed, mounted onto the cast framework, invested, and then pressed. The process ends at 1650. The end result is a fabricated bridge 1500' including three fabricated crowns 1541'-1543'. The bridge 1500' is designed to be installed on three or more abutments along an insertion vector $V_I$.

Anterior Restorations and the Stria of Retzius

Figure 17:
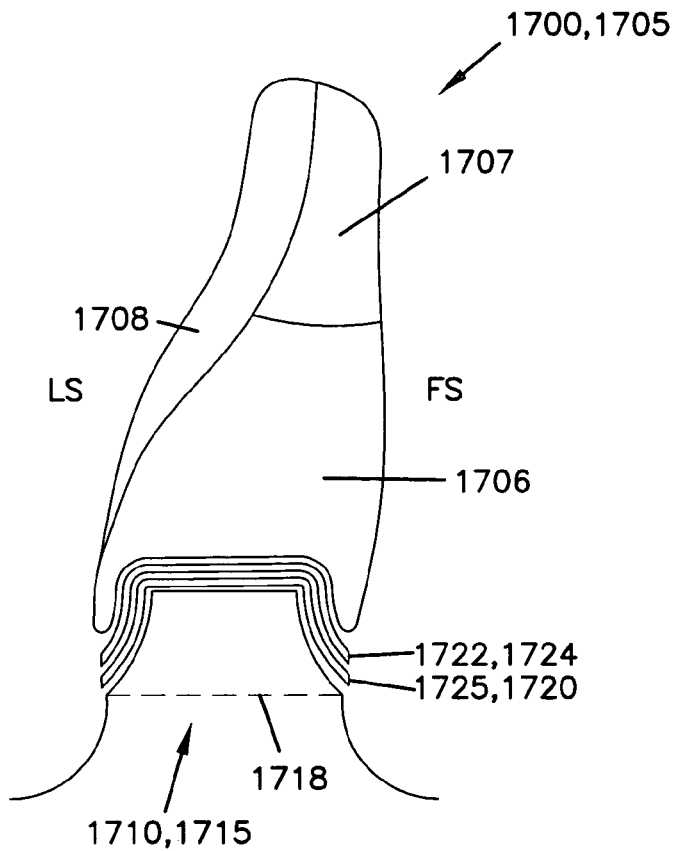
FIG. 17 illustrates a side view of an example electronic model of a restoration for an anterior tooth according to one embodiment of the disclosure.
Figure 18:
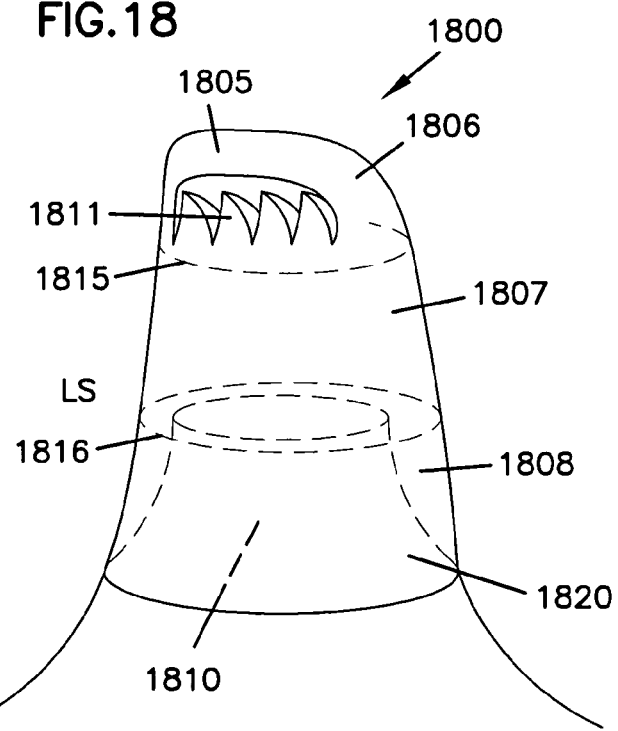
FIG. 18 illustrates a perspective view of the lingual side of an example electronic model of an anterior tooth restoration according to another embodiment of the disclosure.

Referring to FIGS. 17-18, dental appliances including anterior teeth can also be created using electronic modeling. In some embodiments, some appliances such as anterior restorations are formed from one or more shells. FIG. 17 illustrates a side view of an electronic model 1705 of a restoration 1700 for an anterior tooth according to one embodiment of the present disclosure. The electronic model 1705 of the restoration 1700 is shown installed on an electronic model 1725 of a coping 1720. The electronic model 1725 of the coping 1720, which includes an opaque layer 1722, is shown installed on an electronic model 1715 of an abutment 1710.

The restoration model 1705 shown in FIG. 17 includes a first, second, and third shell 1706, 1707, 1708, respectively. The first and second shells 1706, 1707 form the facial surface FS and the third shell 1708 forms the lingual surface LS of the restoration. According to one embodiment, each of the shells 1706-1708 are sequentially printed, mounted onto the abutment, invested, and pressed. The first shell 1706 is pressed onto the coping 1720, opaque layer 1722, or directly onto the abutment 1710. The second shell 1707 is pressed onto a combination of the abutment 1710 and pressed first shell 1706. The third shell 1708 is pressed onto a combination of the abutment 1710, pressed first shell 1706, and pressed second shell 1707. According to another embodiment, each of the shells is pressed separately and later fastened together. Generally, anterior restorations 1700 are formed from between 1 and 6 shells. Typically, anterior restorations 1700 are formed from 2 or 3 shells.

According to one embodiment, the pressed first shell 1706 is formed of the same material as the pressed second shell 1707. Examples of possible pressed shell material include translucent ceramic, opaque ceramic, plastic, glass, and metal. In some embodiments, the pressed third shell 1708 is formed of a different material than the pressed first and second shells 1706, 1707. According to another embodiment, all of the pressed shells 1706-1708 are formed of the same material. According to yet another embodiment, each of the pressed shells 1706-1708 is formed of a different material and each of the materials has a different corresponding color.

FIG. 18 illustrates a perspective view of the lingual side of an electronic model 1805 of an anterior tooth restoration 1800 according to another embodiment of the present disclosure. The electronic model 1805 is divided into a first, second, and third shell 1806, 1807, 1808 and has an outer surface 1820. The first and second shell 1806, 1807 meet at a connecting plane 1815. The second and third shell 1807, 1808 meet at a connecting plane 1816. The third shell 1808 is designed to install onto an abutment 1810. Examples of an abutment 1810 include a coping, an opaque layer on a coping, a natural tooth, and a tooth substitute. In another embodiment, the electronic model 1805 includes a first and second shell (not shown). The first shell 1806 forms the occlusal surface of the restoration 1800 and the second shell forms the installation surface which mates with the abutment 1810.

Figure 19:
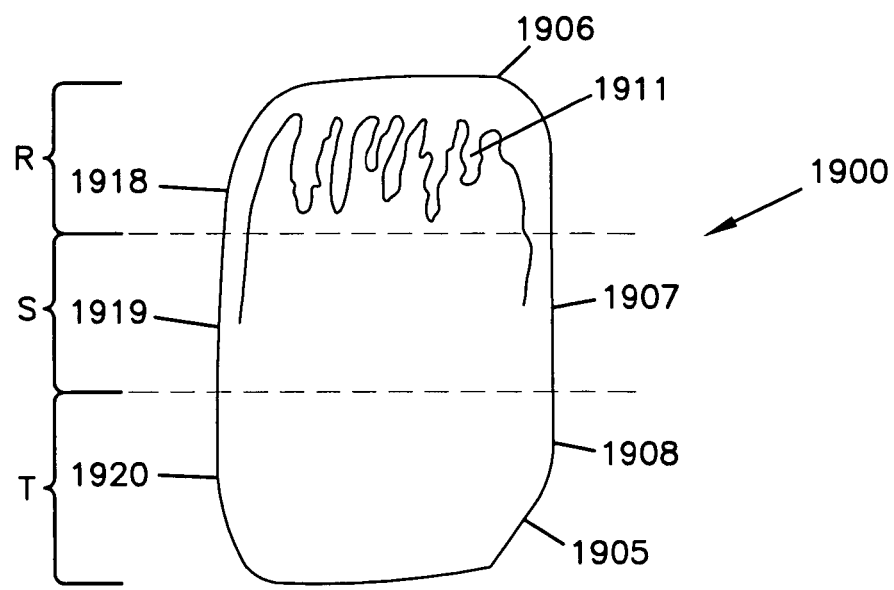
FIG. 19 illustrates a facial view of an anterior restoration in accordance with yet another embodiment of the disclosure.
Figure 20:
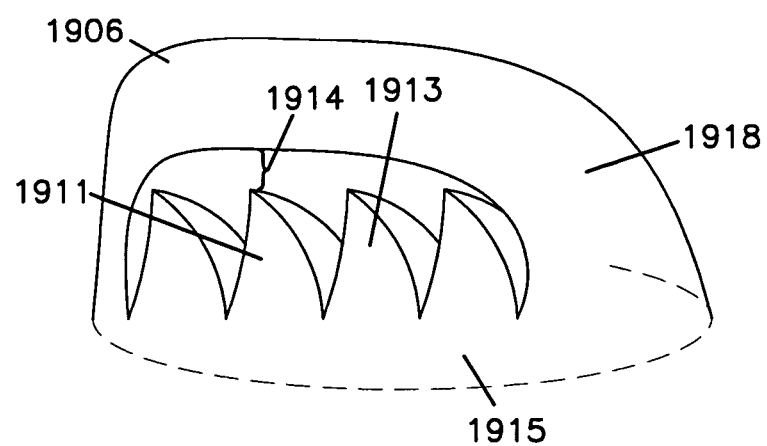
FIG. 20 illustrates a lingual view of a first shell of an anterior restoration having striations in accordance with still yet another embodiment of the disclosure.

Referring now to FIGS. 19 and 20, each shell in one embodiment of the anterior restoration has a different dominant color. FIG. 19 illustrates a facial view of an anterior restoration 1900 including a first, second, and third shell 1906, 1907, 1908, respectively. Each shell 1906-1908 has an outer surface 1918-1920 and each outer surface 1918-1920 has a corresponding color R, S, T, respectively. In one embodiment, the various colors R, S, T result from the different material forming each of the shells 1906-1908. For example, in one embodiment, the third shell 1908 is formed of a darker material than the other two shells 1906, 1907. In another embodiment, different ingots are used for each shell 1906-1908. In yet another embodiment, each shell 1906-1908 is hand painted after being pressed to resemble a natural tooth.

According to one embodiment, the first shell 1906 of the restoration 1900 includes a series of color striations 1911 to mimic the Stria of Retzius of a natural tooth. These striations 1911 are variations in the thickness in the surface of the restoration 1900 that cause color variations in linear patterns (e.g., bands or grooves) over one or more of the outer surfaces 1918-1920 of the restoration 1900. The patterns caused by the striations 1911 are best seen in FIG. 19, in which striations 1911 extend jaggedly along the outer surface 1918 of the first shell 1906.

FIG. 20 illustrates a lingual view of the first shell 1906 having striations 1911. The first shell 1906 has an outer surface 1918 and an attachment surface 1915. The attachment surface 1915 is configured to attach to an attachment surface (not shown) of the second shell 1907. A portion of the outer surface 1918 on the lingual side of the first shell 1906 has been removed to allow a better view of the series of striations 1911.

According to one embodiment, the series of color striations 1911 is formed by generating a hollow shell 1906 including only the attachment surface 1915 and the outer surface 1918. The thicknesses of these surfaces 1915, 1918 are an implementation detail and limited only by the structural limitations of the fabrication materials. Three-dimensional shapes 1913 are then placed within the first shell 1906. According to one embodiment, these shapes 1913 extend between the attachment surface 1915 and the outer surface 1918. According to another embodiment, the shapes 1913 extend up from the attachment surface 1915, but terminate before reaching the outer surface 1918, leaving a gap 1914. In an alternative embodiment, a complete shell (nor shown) is generated and a user or computer software deletes sections from the shell to form a series of striations 1911.

In one embodiment, the three-dimensional shapes 1913 are coupled together. In another embodiment, the shapes 1913 are each separately connected to the attachment surface 1915 of the first shell 1906. In yet another embodiment, the shapes 1913 extend up from the second shell 1907. The attachment surface 1915 of the first shell 1906 is configured to allow the series of shapes 1913 to penetrate the surface 1915. According to another embodiment, the first shell 1906 does not include a bottom surface 1915 and instead includes only the outer surface 1918 to function as a cap over the second shell 1907 and the shapes 1913. According to yet another embodiment, the first shell 1906 is designed to have a first series of color striations 1911 and the second shell 1907 is designed to have a second series of color striations (not shown).

According to some embodiments, each shell 1906-1908 is sequentially rapid prototyped and fabricated using the techniques described above with respect to FIGS. 9-11 and 17. The three-dimensional shapes 1913 are rapid prototyped and pressed along with at least one of the shells 1906-1908 as a part of that shell 1906-1908. In one embodiment, further color variation may be applied manually to the restoration 1900 after pressing using paint, dye, or any other suitable coloration means. In another embodiment, the restoration 1900 is deliberately undersized to enable the outer surface to be created from Feldspathic ceramic one layer at a time.

Material Expansion/Contraction Compensation

Figure 21:
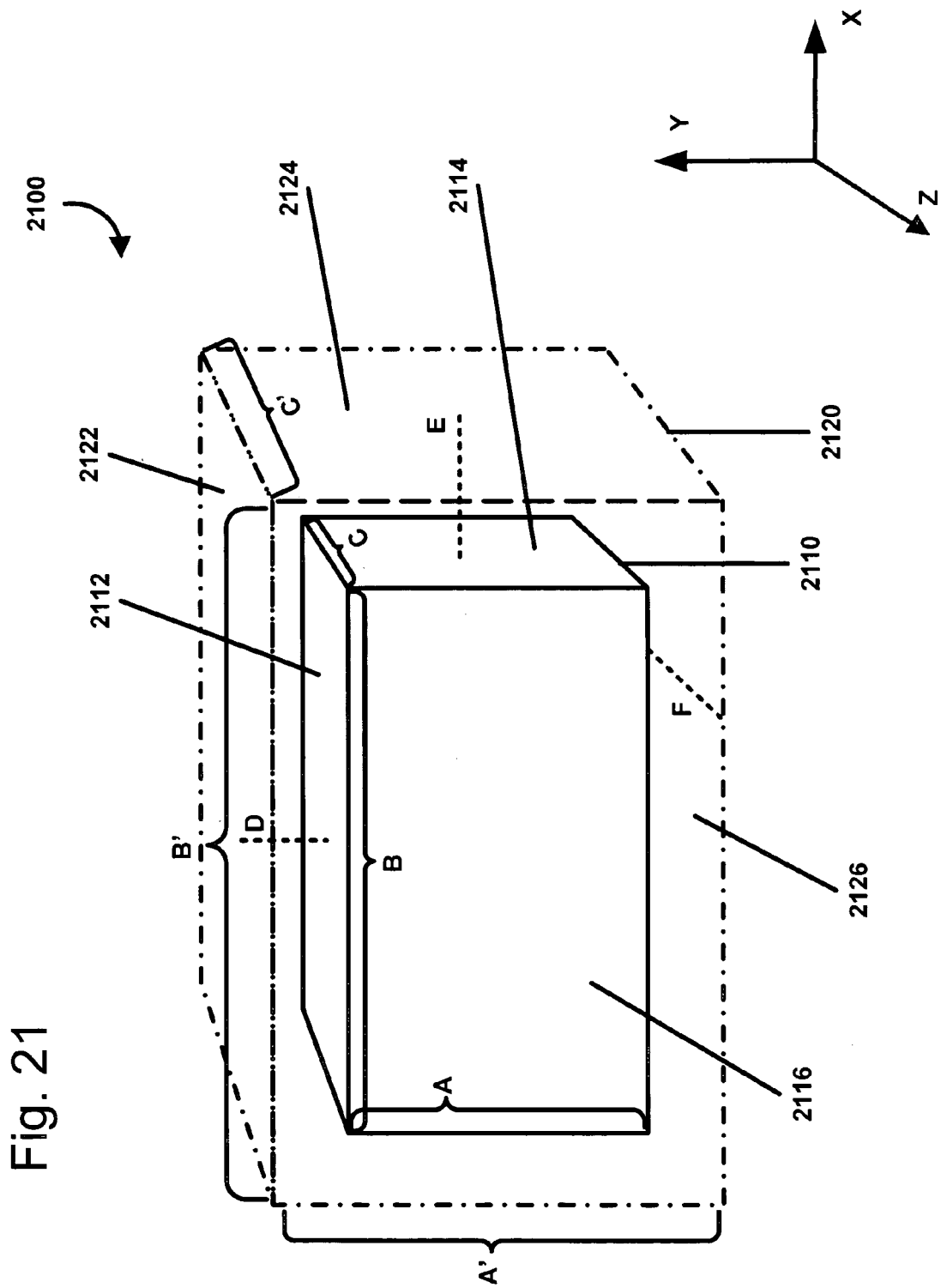
FIG. 21 illustrates a technique to measure a transformation factor or an offset distance for a given material in accordance with one embodiment of the disclosure.
Figure 22:
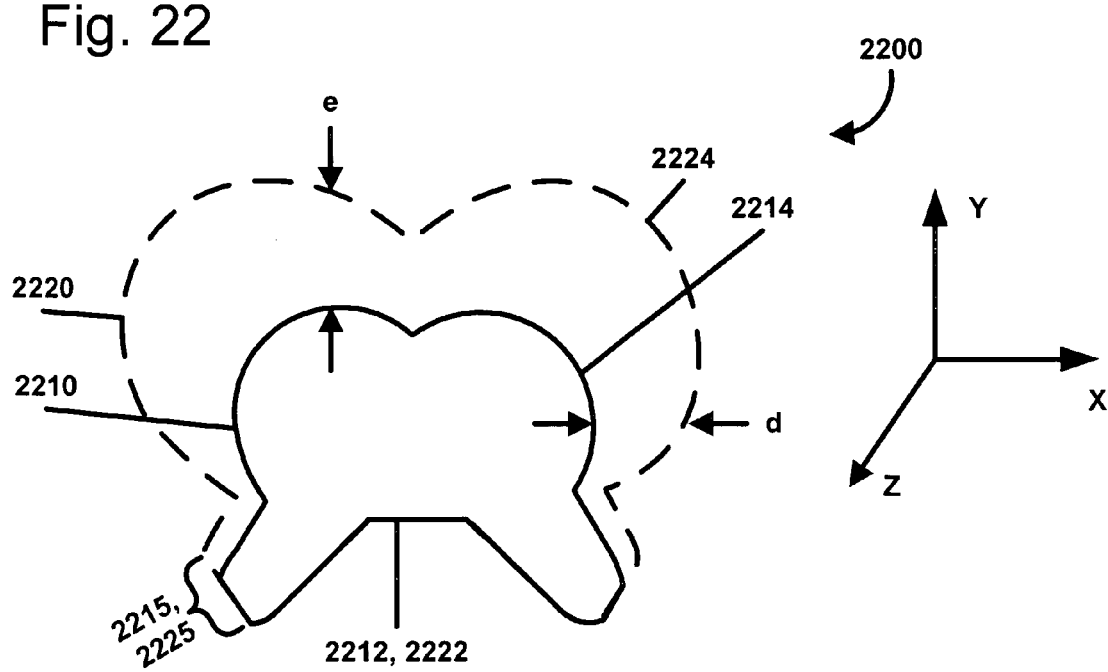
FIG. 22 illustrates an electronic model of a first crown in relation to a desired crown, the first crown to be formed from a material that expands or contracts as a function of thickness.
Figure 23:
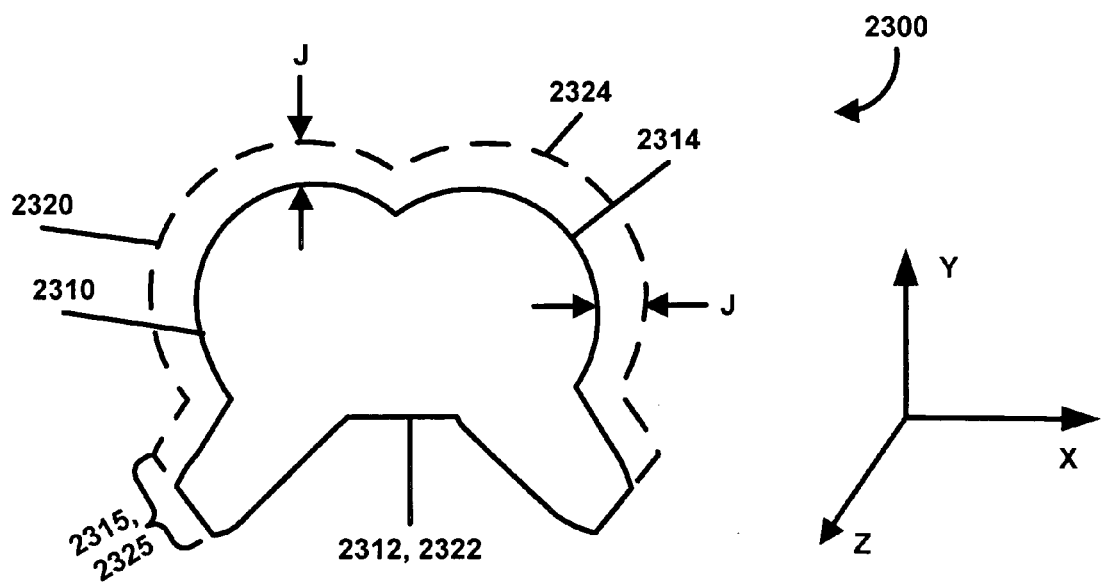
FIG. 23 illustrates an electronic model of a second crown in relation to a desired crown, the second crown to be formed from a material that expands by a constant amount regardless of thickness.

Referring now to FIGS. 21-23, for various reasons, the dimensions of a dental appliance, once fabricated, can differ from the dimensions of the designed electronic model of the appliance. In some cases, the material forming the appliance expands or contracts during the fabrication process. In some embodiments, the investment material recedes from the wax print before fully hardening, leaving a cavity for the ceramic having larger dimensions than the wax print had. The following disclosure provides a technique for obtaining a dental appliance of the desired specifications. The technique generally includes transforming or offsetting the electronic model specifications from the desired dimensions by an amount based on the material being used to fabricate the restoration.

FIG. 21 illustrates a technique to measure a transformation factor or offset distance for a given material. An electronic model 2110 of a three-dimensional shape is shown in FIG. 21 in solid lines. In this embodiment, the displacement of two or more pairs of opposing surfaces 2112, 2114, 2116 will indicate whether the material 2100 expands or contracts by a constant amount or as a function of thickness. However, any three-dimensional shape having non-uniform dimensions can be used in place of a brick.

The electronic model 2110 includes a first side 2112 having a length B and a width C, a second side 2114 having a length A and a width C, and a third side 2116 having a length B and a width A. The electronic model 2110 is used to generate an STL file and rapid prototype a wax print of the brick, which is used in lost-wax casting processes. The resulting brick illustrated in dashed lines, is cast or pressed from a material 2100. The resulting brick 2120 includes a first side 2122 having a length B' and width C', a second side 2124 having a length A' and a width C', and a third side 2126 having a length B' and a width A'. The first, second, and third sides 2122, 2124, and 2126 are displaced by a distance D, E, and F, respectively.

In order to fabricate a cast brick having the desired dimensions A, B, and C, the electronic model of the brick 2110 must first be transformed. To determine the amount by which the electronic model 2110 must be transformed, the dimensions A', B', and C' of the cast brick 2120 are compared with the dimensions A, B, and C of the electronic model 2110. If the material 2100 is found to expand or contract as a function of thickness, such that D≠E, E≠F, or D≠F, then a transformation factor d, e, f, is determined for each dimension x, y, z, respectively, of the electronic model 2110.

An x-component, y-component, and z-component of each position point on the electronic model 2110 is multiplied by the x-dimension transformation factor, y-dimension transformation factor, and z-dimension transformation factor, respectively, thereby transforming the electronic model 1210 into a second electronic model (not shown). This second electronic model, when cast, results in a cast brick having the desired specifications A, B, and C.

In the alternative, if the material 2100 is found to expand evenly over all sides of the brick, such that D=E=F, then an offset distance J is calculated and applied to the x-component, y-component, and z-component of each point on the electronic model 2110.

FIG. 22 illustrates an electronic model of a crown in relation to a desired crown, a crown to be formed from a material that expands or contracts as a function of thickness. The electronic model 2210 necessary to cast the crown 2220 is also illustrated. The crown 2220 is shown in dashed lines and the electronic model 2210 is shown in solid lines. The material 2200 has an x-dimension transformation factor d, a y-dimension transformation factor e, and a z-dimension transformation factor (not shown). Applicants note that FIG. 22 presents an exaggerated depiction of the transformation factors d, e for illustration purposes.

In one embodiment, the inner surface 2222 of the crown 2220 does not expand during the investment process and so the transformation factors d, e are not applied to the inner surface 2212 of the electronic model 2210. In another embodiment, the transformation factors d, e are applied to every point on the electronic model 2210. According to one embodiment, a section 2215 of the exterior surface 2214 of the electronic model 2210 is not displaced according to the transformation factors d, e. This section 2215 is characterized as the base of the crown and is designed so that the dimensions of the surface 2214 on the electronic model 2210 are equal to the dimensions of the external surface 2224 of the desired crown 2220. Therefore, pressing the electronic model 2210 results in excess material located around the base 2225 of the crown 2220, providing extra material with which to perform manual touch-ups.

FIG. 23 illustrates an electronic model of a crown 2320 in relation to a desired crown, the crown 2320 to be formed from a material 2300 that expands by a constant amount regardless of thickness. The amount by which the material 2300 expands is often referred to as the offset distance J. The offset distance J is somewhat exaggerated in FIG. 23 for illustration purposes. The electronic model 2310 is depicted in solid lines and the desired crown 2320 is depicted in dashed lines. In one embodiment, the inner surface 2322 of the desired restoration 2320 does not expand during the investment process and so the offset distance J is not applied to the inner surface 2312 of the electronic model 2310. In another embodiment, the offset distance J is applied to every point on the electronic model 2310. According to yet another embodiment, a section 2315 of the exterior surface 2314 of the electronic model 2310 is not displaced according to the offset distance J. This section 2315 is characterized as the base of the crown and is designed so that the dimensions of the surface 2314 on the electronic model 2310 are equal to the dimensions of the external surface 2324 of the desired crown 2320. Therefore, pressing the electronic model 2310 results in excess material located around the base 2325 of the crown 2320, providing extra material with which to perform manual touchups.

Support Structures

Figure 24:
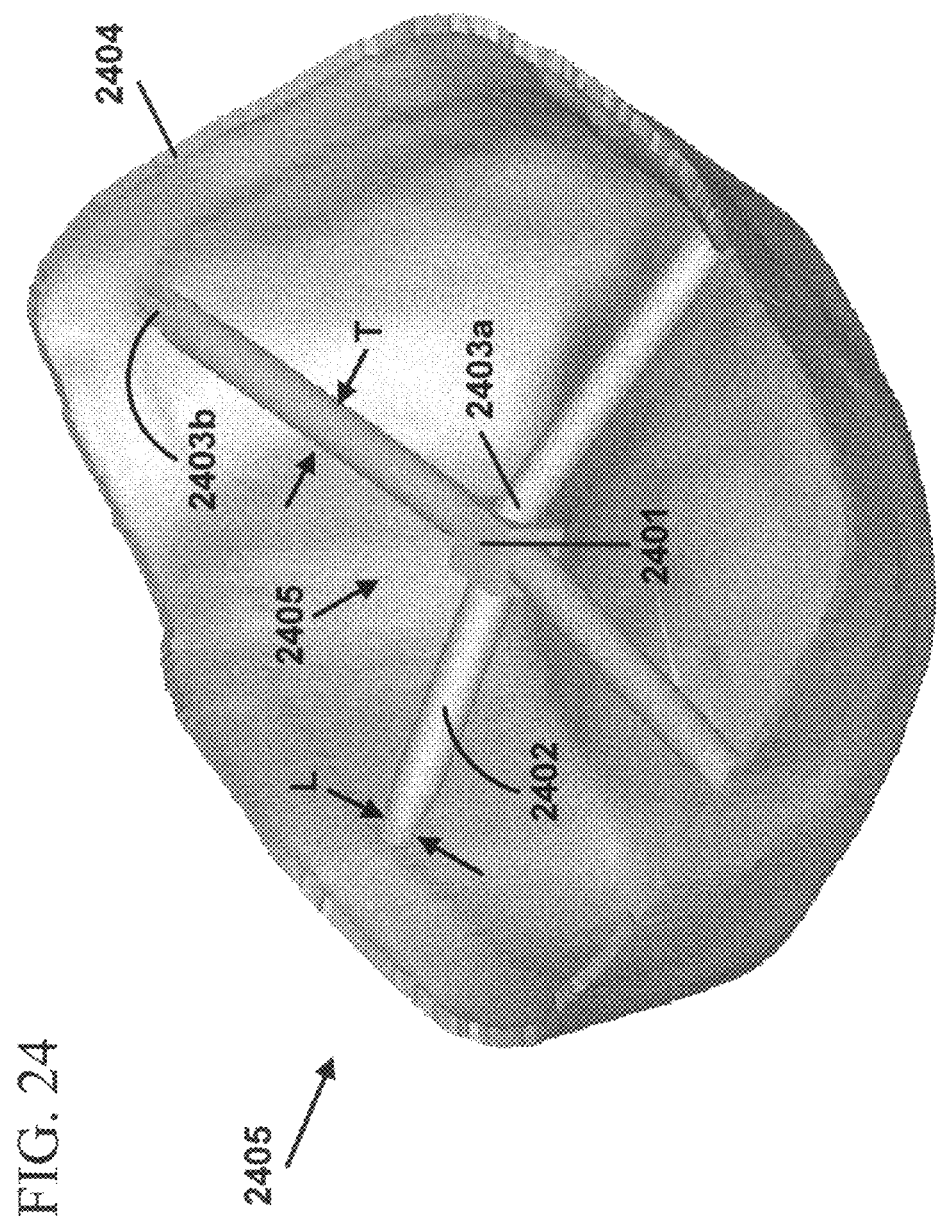
FIG. 24 illustrates an internal support structure for preventing a wax model from warping before being cast or pressed in accordance with one embodiment of the disclosure.
Figure 25:
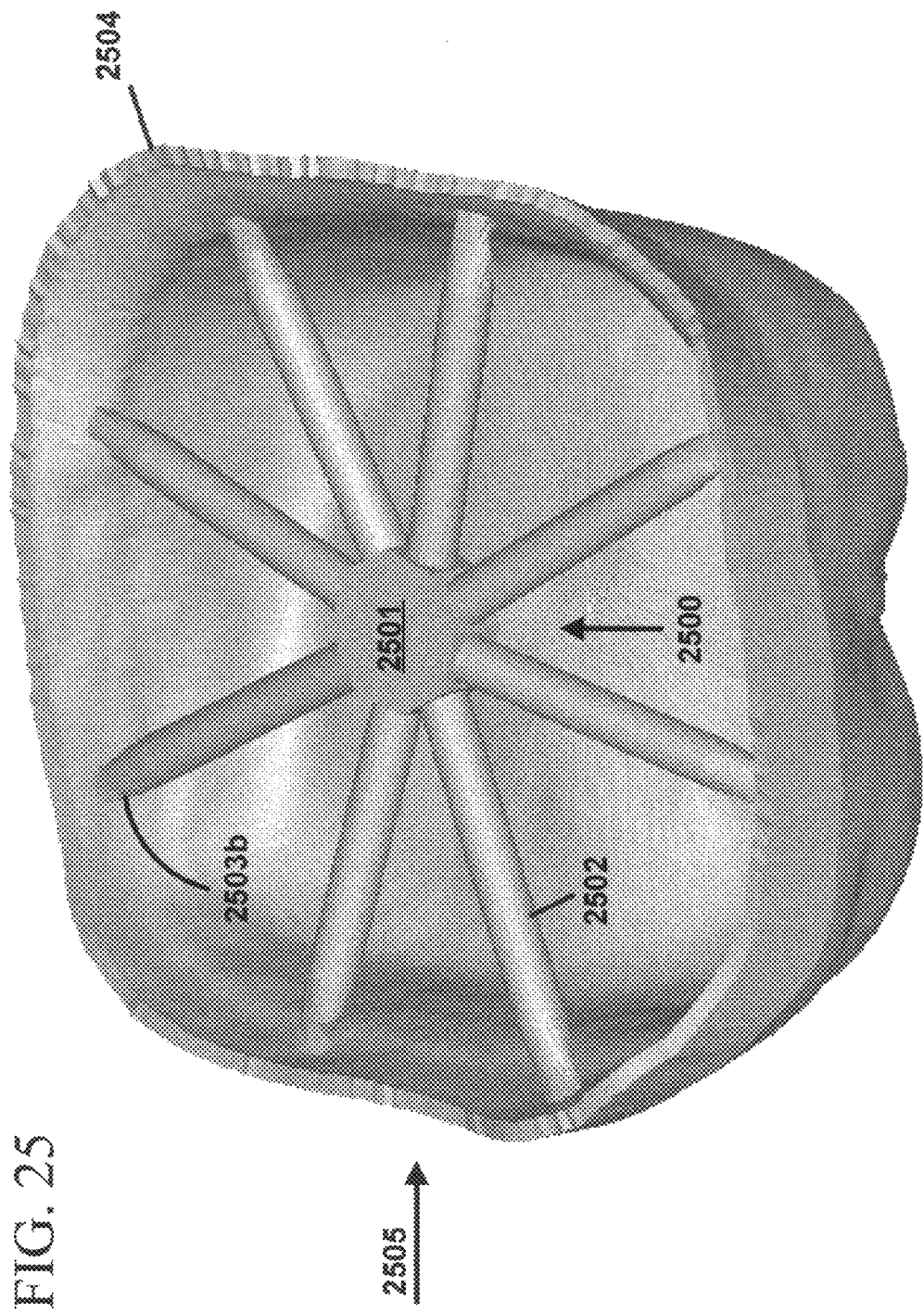
FIG. 25 illustrates an internal support structure including eight spokes in accordance with another embodiment of the disclosure.
Figure 26:
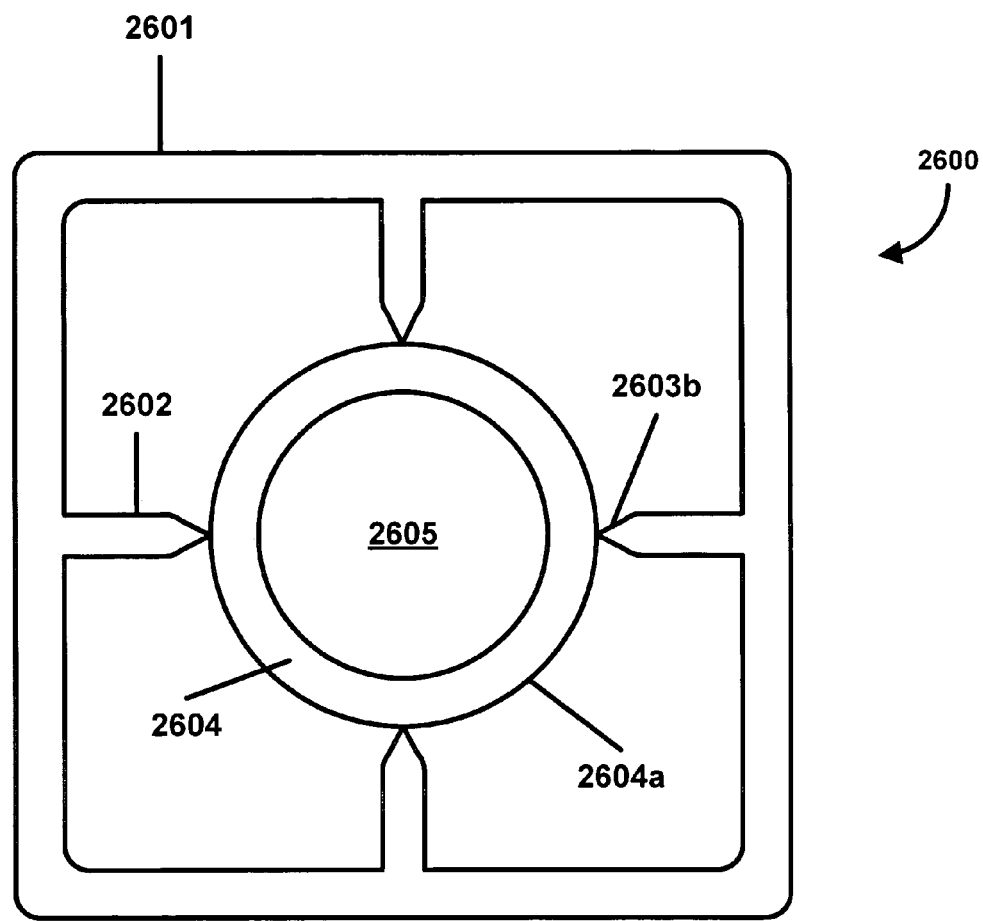
FIG. 26 illustrates an external support structure including four spokes in accordance with yet another embodiment of the disclosure.

Referring now to FIGS. 24, 25, and 26, support structures can be modeled and printed along with wax models of the dental components to minimize deformation of the wax models. Some rapid prototyping machines can only print each layer over an existing surface. Therefore, to make a wax model having overhangs, a second type of wax having a lower melting point than the wax forming the wax model is used as a scaffold. This second type of wax is configured to be dissolved in a solution to remove it from the wax model. Heat is applied to the solution in order to dissolve the wax scaffold. In some example systems, the wax model has a thickness ranging between 0.3 to 0.4 mm. Therefore, the heat applied to dissolve the scaffold would be sufficient to at least partially deform the wax model.

FIG. 24 illustrates an internal support structure for minimizing the deformation of a wax model of a coping substructure. According to another embodiment, the wax model is a ceramic portion of a crown. However, the invention is not limited to these embodiments and the support structure may be used with any wax model. The support structure includes a spacer 2400 supporting the walls 2404 of the wax model 2405.

In some embodiments, the spacer 2400 includes a hub 2401 and spokes 2402. Each spoke 2402 of the spacer 2400 has a first and second end 2403a, 2403b. Each spoke 2402 attaches to the hub 2401 at the first end 2403a and to a portion of the inner surface of the walls 2404 of the wax model 2405 at the second end 2403b. Generally, the spacer 2400 includes between two and twelve spokes 2402. Typically, the spacer 2400 includes eight spokes 2402 as shown in FIG. 25. The size and shape of the hub 2401, 2501 depends upon the number of spokes 2402, 2502 used in the support structure 2400, 2500.

Referring now to FIG. 26, an alternate embodiment of a support structure attaches to an outer surface of the walls of a wax model. FIG. 26 illustrates a wax model 2605 having walls 2604 positioned within an external spacer 2600. The external spacer 2600 includes a frame 2601 and spokes 2602 having attachment ends 2603 which attach to the outer surface 2604a of the walls 2604 of the wax model 2605.

Referring back to FIGS. 24-26, in some embodiments, the second end 2403b, 2503b, 2603b of each spoke 2402, 2502, 2602, which is the end attaching to the wall 2404, 2504, 2604 of the wax model 2405, 2505, 2605 tapers for easier removal. According to one embodiment, the second ends 2403b, 2503b, 2603b taper symmetrically. According to another embodiment, the taper of the second ends 2403b, 2503b, 2603b follows the curve of the walls 2404, 2504, 2604.

According to one embodiment, the placement of the spokes 2402, 2502, 2602 is selected by computer software. According to another embodiment, an operator may use computer software to manually select the position points of the spokes 2402, 2502, 2602 on an electronic image displayed on a display device (e.g., FIG. 3, reference no. 351). In either embodiment, the position points may be manually adjusted after selection using the software.

Generally, the spokes 2402, 2502, 2602 have a thickness T of between 0.25 and 1 mm. Typically, the spokes are 0.5 mm thick. Generally, the second ends 2403b, 2503b, 2603b of the spokes 2402, 2502, 2602 taper to a thickness L of between 0.1 to 0.5 mm. Typically, the second ends 2403b, 2503b, 2603b taper to a thickness L of 0.25 mm.

The spacers 2400, 2500, 2600 are electronically modeled, printed out, and placed in solution along with the wax model 2405, 2505, 2605. In one embodiment, the spacers 2400, 2500, 2600 are removed prior to casting or pressing. Methods of removing the spacers 2400, 2500, 2600 include breaking off or cutting the wax spokes 2402, 2502, 2602 at the second ends 2403b, 2503b, 2603b. However, the invention is not limited to these methods and any suitable method may be used. In another embodiment, the spacers 2400, 2500, 2600 are removed after casting. In this case, the spacers 2400, 2500, 2600 are cast or pressed along with the wax models 2405, 2505, 2605. The cast spacers are then removed from the cast model.

While the above embodiments of the present invention describe a system and method for constructing dental restorations, bridges, and implants using a lost-wax process, one skilled in the art will recognize that other methods of manufacture of the dental devices are possible. The present invention allows fabrication of fixed and removable prosthodontic prosthesis such as copings, crowns, inlays, onlays, veneers, bridges, frameworks, implants, abutments, surgical stents, full or partial dentures and other hybrid fixed prosthesis for dental applications. Other dental and orthodontic appliances may also readily be constructed in accordance of the present invention. As such, as long as the manufacturing process utilizes electronic models for impressions of patient's teeth and corresponding electronic models for the dental appliances, the present invention would be useable in other manufacturing methodologies. It is to be understood that other embodiments may be utilized and operational changes may be made without departing from the scope of the present invention.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto.

We claim:

1. A method for constructing a dental appliance having multiple components, the method comprising:
   generating a first electronic model of a first dental component of the dental appliance;
   rapid prototyping a first wax model of the first dental component based on the first electronic model of the first dental component;
   casting a first fabricated first dental component using the first wax model;
   obtaining a second electronic model representing the first fabricated dental component and a preparation site on which the first fabricated dental component is mounted; wherein obtaining the second electronic model comprises: mounting the first fabricated dental component to a study cast representing a patient dentition including the preparation site; scanning the study cast and the first fabricated dental component to obtain three-dimensional data; and generating the second electronic model based on the three-dimensional data;
   generating a third electronic model of a second dental component of the dental appliance, the third electronic model being designed to fit with the second electronic model; wherein the method of generating the third electronic model of the second dental component further comprises superimposing the third electronic model over the second electronic model;
   rapid prototyping a second wax model of the second dental component based on the third electronic model of the second dental component; and
   pressing a second fabricated dental component onto the first fabricated dental component using the second wax model.

2. The method of claim 1, further comprising:
   designing an electronic model of a support structure designed to support the first wax model, wherein rapid prototyping the first wax model of the first dental component comprises rapid prototyping the support structure and the first wax model as a unitary piece.

3. The method of claim 1, further comprising:
designing a plurality of electronic models, each electronic model representing one of a plurality of bridge components;
printing wax models of each of the plurality of bridge components based on the corresponding electronic models;
casting or pressing each of the wax models of the plurality of bridge components to form fabricated bridge components; and
combining the fabricated bridge components onto the dental appliance to form a dental bridge.

4. The method of claim 1, further comprising:
transforming at least one electronic model selected from the group consisting of the first electronic model and the third electronic model such that dimensions of the transformed electronic model differ from desired dimensions of the dental appliance by a transformation factor; and
fabricating the dental appliance using a material, the material changing in dimension during fabrication according to the transformation factor.

5. The method of claim 1, wherein the first fabricated dental component is formed from a first material and the second fabricated dental component is formed from a second material.

6. The method of claim 5, wherein the first material differs from the second material in at least one of color, texture, opacity, and transformation factor.

7. The method of claim 1, wherein the first dental component is a coping.

8. The method of claim 1, wherein the second dental component is a crown.

9. The method of claim 1, wherein the second dental component is a crown shell.

10. The method of claim 7, wherein generating the first electronic model of a coping includes:
generating a first offset mesh designed to mate with a surface of an abutment of a patient;
generating an exterior mesh representing an exterior surface at a desired position in relation to the offset mesh; and
merging the offset mesh with the exterior mesh.

11. The method of claim 10, wherein the abutment includes one of a natural tooth and an implanted tooth substitute.

12. The method of claim 7, wherein the coping wax model is formed from wax and wherein casting the coping includes casting the wax model of the coping using a lost-wax technique to form a metal coping.

13. The method of claim 7, further comprising the step of applying an opaque coating to the coping.

14. The method of claim 10, wherein generating an exterior mesh includes generating a collar to extend at least partially around the coping.

15. The method of claim 8, wherein generating the third electronic model includes designing a series of three-dimensional shapes on the third electronic model to form color striations on the dental appliance.

16. The method of claim 8, wherein generating the third electronic model of a crown includes:
generating a second offset mesh designed to mate with an exterior surface of the fabricated first component;
selecting an occlusal surface mesh;
transforming the occlusal surface mesh to a desired location adjacent the second offset mesh;
generating a side mesh between the occlusal surface mesh and the second offset mesh; and
merging the offset mesh, the occlusal surface mesh, and the side mesh.

17. The method of claim 8, wherein the first dental component is an abutment and the method further includes:
designing an electronic model of a post for implanting into an alveolar bone of a patient;
printing a post wax model based on the electronic model of the post; and
casting or pressing the post wax model onto the dental appliance to form a dental implant.

18. The method of claim 8, wherein the fabricated crown is formed from one of ceramic, metal, resin, plastic, composite, and porcelain.

19. The method of claim 8, wherein generating the second electronic model of a crown includes:
designing one electronic model of a first crown shell; and
designing another electronic model of a second crown shell.

20. The method of claim 19, further comprising forming a series of color striations in at least one of the electronic models of the first and second crown shells.

21. The method of claim 19, wherein printing the wax model based on the electronic model of the crown includes at least one of:
printing a first crown shell wax model based on the electronic model of the first crown shell; and
printing a second crown shell wax model based on the electronic model of the second crown shell.

22. The method of claim 20, wherein pressing the wax model of the crown onto the fabricated first component includes at least one of:
pressing the first crown shell onto the fabricated first component using the first crown shell wax model to form a partial dental appliance; and
pressing the second crown shell onto the partial dental appliance using the second crown shell wax model to form the dental appliance.

23. The method of claim 16, wherein generating a second offset mesh includes:
mounting the fabricated first component onto a study cast representing at least an abutment such that the fabricated first component forms part of the abutment;
scanning the study cast to generate an electronic model of the abutment including the fabricated first component; and
designing the second offset mesh to mate with the electronic model of the abutment.

24. The method of claim 16, wherein selecting the occlusal surface mesh includes selecting the occlusal surface mesh from a library of occlusal surface meshes.

25. The method of claim 16, wherein transforming the occlusal surface mesh includes at least one of: positioning the occlusal surface mesh, orientating the occlusal surface mesh, sizing the occlusal surface mesh, and deforming the occlusal surface mesh or a portion thereof.

26. The method of claim 1, further comprising applying an opaque coating to the first fabricated dental component prior to scanning.

* * * * *